(12) United States Patent
Hansman et al.

(10) Patent No.: US 11,555,063 B2
(45) Date of Patent: Jan. 17, 2023

(54) NOROVIRUS ANTIBODIES

(71) Applicants: Universität Heidelberg, Heidelberg (DE); Deutsches Krebsforschungszentrum, Heidelberg (DE)

(72) Inventors: Grant Hansman, Heidelberg (DE); Anna Koromyslova, Dossenheim (DE)

(73) Assignees: Universität Heidelberg, Heidelberg (DE); Deutsches Krebsforschungszentrum, Heidelberg (DE)

(*) Notice: Subject to any disclaimer, the term of this patent is extended or adjusted under 35 U.S.C. 154(b) by 140 days.

(21) Appl. No.: 16/649,345

(22) PCT Filed: Sep. 19, 2018

(86) PCT No.: PCT/EP2018/075324
§ 371 (c)(1),
(2) Date: Mar. 20, 2020

(87) PCT Pub. No.: WO2019/057755
PCT Pub. Date: Mar. 28, 2019

(65) Prior Publication Data
US 2020/0231656 A1    Jul. 23, 2020

(30) Foreign Application Priority Data
Sep. 20, 2017 (EP) .................... 17192166

(51) Int. Cl.
*C07K 16/10* (2006.01)
(52) U.S. Cl.
CPC ........ *C07K 16/10* (2013.01); *C07K 2317/565* (2013.01); *C07K 2317/569* (2013.01)
(58) Field of Classification Search
None
See application file for complete search history.

(56) References Cited

U.S. PATENT DOCUMENTS 5,591,828 A    1/1997    Bosslet et al.

FOREIGN PATENT DOCUMENTS

| EP | 0404097 A2 | 6/1990 | |
|---|---|---|---|
| EP | 2757111 A1 | 7/2014 | |
| WO | 199301161 A1 | 1/1993 | |
| WO | 2016059113 A1 | 4/2016 | |
| WO | WO-2016059113 A1 * | 4/2016 | ............. C07K 16/10 |

OTHER PUBLICATIONS

Koromyslova et al., J Virol. Mar. 2015;89(5):2718-30. doi: 10.1128/JVI.03176-14. Epub Dec. 17, 2014.*
Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Ghahroudi et al., FEBS Letters Sep. 15, 1997; 414(3): 521-526.*
Huo et al., Virus Res. Jun. 2, 2015;204:1-5. doi: 10.1016/j.virusres. 2015.04.009. Epub Apr. 17, 2015. PMID: 25892715.*
Paul D. Adams et al.; PHENIX: A Comprehensive Python-Based System for Macromolecular Structure Solution; Acta Crystallographica Section D; 2010; 9 pages; vol. D66.
Sue E. Crawford et al.; Mapping Broadly Reactive Norovirus Genogroup I and II Monoclonal Antibodies; Clinical and Vaccine Immunology; Feb. 2015; 10 pages; vol. 22, No. 2.
Sylvie Y. Doerflinger et al.; Human Norovirus Evolution in a Chronically Infected Host; American Society of Microbiology; mSphere; Mar./Apr. 2017; 14 pages; vol. 2, Issue 2.
P. Emsley et al.; Features and Development of Coot; Acta Crystallographica Section D; Biological Crystallography; 2010; 16 pages; vol. D66.
G. S. Hansman et al.; Cross-Reactivity Among Sapovirus Recombinant Capsid Proteins; Archives of Virology; 2005; 16 pages; vol. 150.
Grant S. Hansman et al.; Genetic and Antigenic Diversity Among Noroviruses; Journal of General Virology; 2006; 11 pages; vol. 87.
Grant S. Hansman et al.; Outbreak of Gastroenteritis Due to Sapovirus; Journal of Clinical Microbiology; Apr. 2007; 3 pages; vol. 45, No. 4.
Grant S. Hansman et al.; Structural Basis for Broad Detection of Genogroup II Noroviruses by a Monclonal Antibody That Binds to a Site Occluded in the Viral Particle; Journal of Virology; Jan. 25, 2012; 13 pages.
Philipp Holliger; "Diabodies": Small Bivalent and Bispecific Antibody Fragments; Proc. Natl. Acad. Sci. USA; Jul. 1993; 5 pages; vol. 90.
Peter J. Hudson et al.; Engineered Antibodies; Nature Medicine; Jan. 2003; 6 pages; vol. 9, No. 1.
Wolfgang Kabsch; XDS; Acta Crystallographica Section D; Biological Crystallography; 2010; 8 pages; vol. D66.

(Continued)

*Primary Examiner* — Michael Szperka
(74) *Attorney, Agent, or Firm* — Taft Stettinius & Hollister LLP

(57) ABSTRACT

The present invention relates to a binding polypeptide specifically binding to an epitope comprised in an amino acid sequence corresponding to amino acids 250 to 300 of the norovirus genotype II.10 capsid polypeptide, and to a polynucleotide encoding the same. The present invention further relates to a composition comprising the binding polypeptide according to the present invention and a carrier, and to the binding polypeptide or the composition comprising the same use in diagnosis and/or for use in medicine. Further more, the present invention relates to kits, devices, vaccines, methods, and uses related to the binding polypeptide of the present invention.

12 Claims, 8 Drawing Sheets

Figure 1:
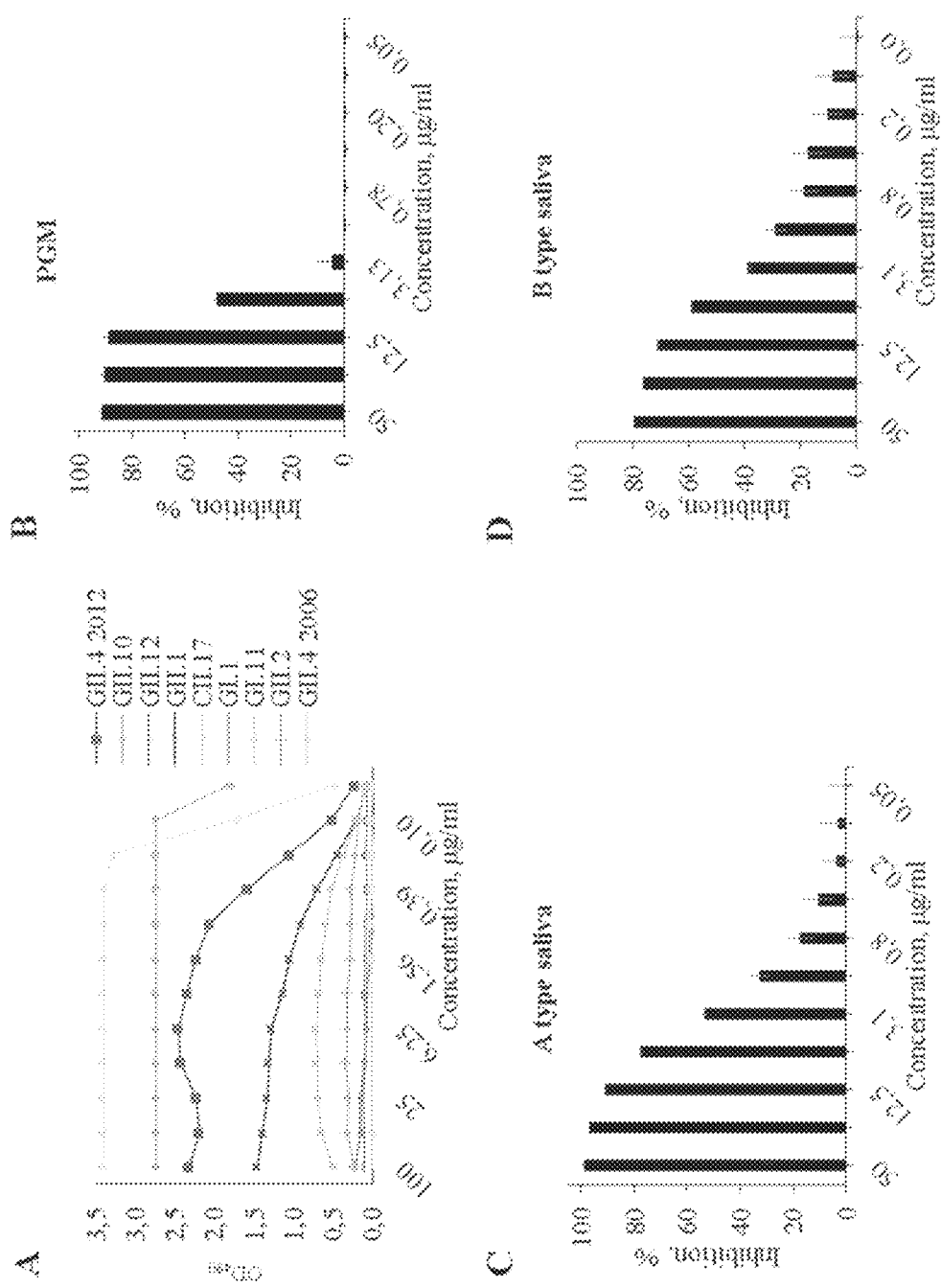

Specification includes a Sequence Listing.

(56) References Cited

OTHER PUBLICATIONS

Anna D. Koromyslova et al.; Nanobodies Targeting Norovirus Capsid Reveal Functional Epitopes and Potential Mechanisms of Neutralization; 1100-Pos Board B9; Feb. 19, 2018; 1 page.
Anna D. Koromyslova et al.; Nanobody Binding to a Conserved Epitope Promotes Norovirus Particle Disassembly; Journal of Virology; Mar. 2015; 13 pages; vol. 89, No. 5.
Konstantin V. Korotkov et al.; Crystal Stmcture of the N-Terminal Domain of the Secretin GspD from ETEC Determined with the Assistance of a Nanobody; NIH Public Access; Stmcture; Feb. 13, 2009; 21 pages; vol. 17, No. 2.
Baijun Kou et al.; Characterization of Cross-Reactive Norovirus-Specific Monoclonal Antibodies; Clinical and Vaccine Immunology; Feb. 2015; 8 pages; vol. 22, No. 2.
Annelies Kroneman et al.; Proposal for a Unified Norovirus Nomenclature and Genotyping; HHS Public Access; Arch Virol.; Oct. 2013; 18 pages; vol. 158, No. 10.
Xiao Li et al.; Characterization of a Cross-Reactive Monoclonal Antibody Against Norovims Genogroups I, II, III and V; Elsevier; Virus Research; 2010; 6 pages; vol. 151.
Xiao Li et al.; Identification and Characterization of a Native Epitope Common to Norovirus Strains GII/4, GII/7 and GII/8; Elsevier; Virus Research; 2009; 6 pages; vol. 140.
Airlie J. McCoy et al.; Phaser Crystallographic Software; Journal of Applied Crystallography; 2007; 17 pages; vol. 40.
Tracy Dewese Parker et al.; Identification of Genogroup I and Genogroup II Broadly Reactive Epitopes on the Norovirus Capsid; Journal of Virology; Jun. 2005; 8 pages; vol. 79, No. 12.
Gabriel I. Parra et al.; Identification of a Broadly Cross-Reactive Epitope in the Inner Shell of the Norovirus Capsid; PLOS One; Jun. 2013; 7 pages; vol. 8, No. 6.
B. V. Venkataram Prasad et al.; X-ray Crystallographic Structure of the Norwalk Virus Capsid; Science; Oct. 8, 1999; 5 pages; vol. 286.
Tomoyuki Shiota et al.; Characterization of a Broadly Reactive Monoclonal Antibody Against Norovirus Genogroups I and II: Recognition of a Novel Conformational Epitope; Journal of Virology; Nov. 2007; 9 pages.
Thomas James Smith; Structural Studies on Antibody Recognition and Neutralization of Viruses; NIH Public Access; Curr Opin Virol.; Aug. 1, 2011; 12 pages; vol. 1, No. 2.
Stefan Weichert et al.; Structural Basis for Norovirus Inhibition by Human Milk Oligosaccharides; Journal of Virology; May 2016; 6 pages; vol. 90, No. 9.
Tomoko Yoda et al.; Precise Characterization of Norovirus (Norwalk-Like Virus)-Specific Monoclonal Antibodies with Broad Reactivity; Journal of Clinical Microbiology; Jun. 2003; 5 pages; vol. 41, No. 6.
International Search Report; European Patent Office; International Application No. PCT/EP2018/075324; dated Nov. 20, 2018; 3 pages.
Written Opinion of the International Searching Authority; European Patent Office; International Application No. PCT/EP2018/075324; dated Nov. 20, 2018; 8 pages.

* cited by examiner

SEQUENCE LISTING

<160> NUMBER OF SEQ ID NOS: 22

<210> SEQ ID NO 1
<211> LENGTH: 548
<212> TYPE: PRT
<213> ORGANISM: norovirus genotype II.10

<400> SEQUENCE: 1

```
Met Lys Met Ala Ser Asn Asp Ala Ala Pro Ser Asn Asp Gly Ala Ala
1               5                   10                  15

Gly Leu Val Pro Glu Ser Asn Asn Glu Val Met Ala Leu Glu Pro Val
            20                  25                  30

Ala Gly Ala Ser Leu Ala Ala Pro Val Thr Gly Gln Thr Asn Ile Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Met Glu Val Gln Ile Met Leu Ala Gly Asn
            100                 105                 110

Ala Phe Thr Ala Gly Lys Leu Ile Phe Ala Ala Val Pro Pro His Phe
        115                 120                 125

Pro Ile Glu Asn Leu Ser Pro Pro Gln Ile Thr Met Phe Pro His Val
    130                 135                 140

Ile Ile Asp Val Arg Thr Leu Glu Pro Val Leu Leu Pro Met Pro Asp
145                 150                 155                 160

Ile Arg Asn Ser Phe Phe His Phe Ile Gln Arg Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Asp Phe Thr Tyr Leu Val Pro Pro Thr Val Glu Ser Lys Ser
    210                 215                 220

Lys Pro Phe Thr Leu Pro Ile Leu Thr Leu Gly Glu Leu Thr Asn Ser
225                 230                 235                 240

Arg Phe Pro Leu Pro Ile Asp Val Leu Tyr Thr Asn Pro Asn Glu Ser
                245                 250                 255

Ala Ile Val Gln Cys Gln Asn Gly Arg Cys Thr Leu Asp Gly Glu Leu
            260                 265                 270

Gln Gly Thr Thr Gln Leu Leu Pro Thr Gly Ile Cys Ala Phe Arg Gly
        275                 280                 285

Lys Val Thr Gln Gln Val Gln Asp Glu His Arg Gly Thr His Trp Asn
    290                 295                 300

Met Thr Val Thr Asn Leu Asn Gly Thr Pro Phe Asp Pro Thr Glu Asp
305                 310                 315                 320

Val Pro Ala Pro Leu Gly Thr Pro Asp Phe Ser Gly Gln Ile Tyr Gly
                325                 330                 335

Val Ile Ser Gln Arg Asn Thr Asn Thr Val Pro Gly Glu Gly Asn Leu
            340                 345                 350

Pro Ala Asn Arg Ala His Glu Ala Val Ile Ala Thr Tyr Ser Pro Lys
        355                 360                 365
```

-continued

```
Phe Thr Pro Lys Leu Gly Asn Ile Gln Phe Ser Thr Trp Glu Thr Gln
    370                 375                 380

Asp Val Ser Ser Gly Gln Pro Thr Lys Phe Thr Pro Val Gly Leu Ala
385                 390                 395                 400

Ser Val Asp Ala Asn Ser His Phe Asp Gln Trp Thr Leu Pro Ser Tyr
                405                 410                 415

Ser Gly Ala Leu Thr Leu Asn Met Asn Leu Ala Pro Ser Val Ala Pro
            420                 425                 430

Val Phe Pro Gly Glu Cys Leu Leu Phe Phe Arg Ser Phe Ile Pro Leu
        435                 440                 445

Lys Gly Gly Tyr Gly Asn Pro Ala Ile Asp Cys Leu Met Pro Gln Glu
    450                 455                 460

Trp Val Gln His Leu Tyr Gln Glu Ser Ala Pro Ser Leu Ser Asp Val
465                 470                 475                 480

Ala Leu Val Arg Tyr Val Asn Pro Glu Thr Gly Arg Thr Leu Phe Glu
                485                 490                 495

Ala Lys Leu His Arg Asn Gly Phe Leu Thr Val Ala Arg Asn Ser Ala
            500                 505                 510

Gly Pro Val Val Ala Pro Thr Asn Gly Tyr Phe Arg Phe Asp Ser Trp
        515                 520                 525

Val Asn Gln Phe Tyr Thr Leu Ala Pro Met Gly Asn Gly Ser Gly Arg
    530                 535                 540

Arg Arg Met Gln
545

<210> SEQ ID NO 2
<211> LENGTH: 51
<212> TYPE: PRT
<213> ORGANISM: norovirus genotype II.10

<400> SEQUENCE: 2

Tyr Thr Asn Pro Asn Glu Ser Ala Ile Val Gln Cys Gln Asn Gly Arg
1               5                   10                  15

Cys Thr Leu Asp Gly Glu Leu Gln Gly Thr Thr Gln Leu Leu Pro Thr
            20                  25                  30

Gly Ile Cys Ala Phe Arg Gly Lys Val Thr Gln Gln Val Gln Asp Glu
        35                  40                  45

His Arg Gly
    50

<210> SEQ ID NO 3
<211> LENGTH: 21
<212> TYPE: PRT
<213> ORGANISM: norovirus genotype II.10

<400> SEQUENCE: 3

Gln Cys Gln Asn Gly Arg Cys Thr Leu Asp Gly Glu Leu Gln Gly Thr
1               5                   10                  15

Thr Gln Leu Leu Pro
            20

<210> SEQ ID NO 4
<211> LENGTH: 8
<212> TYPE: PRT
<213> ORGANISM: norovirus genotype II.10

<400> SEQUENCE: 4

Asp Gly Glu Leu Gln Gly Thr Thr
```

```
1               5

<210> SEQ ID NO 5
<211> LENGTH: 8
<212> TYPE: PRT
<213> ORGANISM: Artificial
<220> FEATURE:
<223> OTHER INFORMATION: epitope consensus 1
<220> FEATURE:
<221> NAME/KEY: MISC_FEATURE
<222> LOCATION: (1)..(1)
<223> OTHER INFORMATION: acidic amino acid, E or D
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: acidic amino acid, E or D
<220> FEATURE:
<221> NAME/KEY: MISC_FEATURE
<222> LOCATION: (4)..(4)
<223> OTHER INFORMATION: hydrophobic amino acid, G, A, V, or I
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: hydrophobic amino acid, G, A, V, or I
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: S or T

<400> SEQUENCE: 5

Xaa Xaa Xaa Xaa Xaa Xaa Xaa Xaa
1               5

<210> SEQ ID NO 6
<211> LENGTH: 8
<212> TYPE: PRT
<213> ORGANISM: Artificial
<220> FEATURE:
<223> OTHER INFORMATION: epitope 1, consensus 2
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (7)..(7)
<223> OTHER INFORMATION: any amino acid

<400> SEQUENCE: 6

Asp Xaa Glu Leu Xaa Gly Xaa Thr
1               5

<210> SEQ ID NO 7
<211> LENGTH: 41
<212> TYPE: PRT
<213> ORGANISM: norovirus genotype II.10

<400> SEQUENCE: 7
```

-continued

Gly Gly Tyr Gly Asn Pro Ala Ile Asp Cys Leu Met Pro Gln Glu Trp
1               5                   10                  15

Val Gln His Leu Tyr Gln Glu Ser Ala Pro Ser Leu Ser Asp Val Ala
            20                  25                  30

Leu Val Arg Tyr Val Asn Pro Glu Thr
        35                  40

<210> SEQ ID NO 8
<211> LENGTH: 19
<212> TYPE: PRT
<213> ORGANISM: norovirus genotype II.10

<400> SEQUENCE: 8

Tyr Gln Glu Ser Ala Pro Ser Leu Ser Asp Val Ala Leu Val Arg Tyr
1               5                   10                  15

Val Asn Pro

<210> SEQ ID NO 9
<211> LENGTH: 18
<212> TYPE: PRT
<213> ORGANISM: Artificial
<220> FEATURE:
<223> OTHER INFORMATION: epitope 2 consensus 1
<220> FEATURE:
<221> NAME/KEY: misc_feature
<222> LOCATION: (1)..(1)
<223> OTHER INFORMATION: N or Q
<220> FEATURE:
<221> NAME/KEY: misc_feature
<222> LOCATION: (2)..(2)
<223> OTHER INFORMATION: D or E
<220> FEATURE:
<221> NAME/KEY: misc_feature
<222> LOCATION: (3)..(17)
<223> OTHER INFORMATION: x = any amino acid

<400> SEQUENCE: 9

Xaa Xaa Xaa Xaa Xaa Xaa Xaa Xaa Xaa Xaa Xaa Xaa Xaa Xaa Xaa Xaa
1               5                   10                  15

Xaa Pro

<210> SEQ ID NO 10
<211> LENGTH: 19
<212> TYPE: PRT
<213> ORGANISM: Artificial
<220> FEATURE:
<223> OTHER INFORMATION: epitope 2 consensus 2
<220> FEATURE:
<221> NAME/KEY: misc_feature
<222> LOCATION: (4)..(5)
<223> OTHER INFORMATION: x = any amino acid
<220> FEATURE:
<221> NAME/KEY: misc_feature
<222> LOCATION: (7)..(18)
<223> OTHER INFORMATION: x = any amino acid

<400> SEQUENCE: 10

Tyr Gln Glu Ser Xaa Pro Xaa Xaa Xaa Xaa Xaa Xaa Xaa Xaa Xaa Xaa
1               5                   10                  15

Xaa Xaa Pro

<210> SEQ ID NO 11
<211> LENGTH: 115
<212> TYPE: PRT
<213> ORGANISM: Vicugna pacos

<400> SEQUENCE: 11

Gln Val Gln Leu Gln Glu Ser Gly Gly Leu Val Gln Pro Gly Gly
1               5                   10                  15

Ser Leu Arg Leu Ser Cys Thr Ala Pro Arg Ile Ile Phe Phe Met Tyr
            20                  25                  30

Asp Val Gly Trp Tyr Arg Gln Ala Pro Glu Lys Gln Arg Glu Leu Val
                35                  40                  45

Ala Gln Ile Asn Ser Asp Val Ser Thr Lys Tyr Ala Asp Ser Val Lys
        50                  55                  60

Gly Arg Phe Thr Ile Ser Arg Asp Asn Ala Lys Arg Thr Val Tyr Leu
65                  70                  75                  80

Gln Met Asn Asp Leu Lys Pro Glu Asp Ala Ala Val Tyr Tyr Cys Asn
                85                  90                  95

Val Arg Arg Ala Ser Ala Asp Tyr Trp Gly Gln Gly Thr Gln Val Thr
            100                 105                 110

Val Ser Ser
        115

<210> SEQ ID NO 12
<211> LENGTH: 345
<212> TYPE: DNA
<213> ORGANISM: Vicugna pacos

<400> SEQUENCE: 12
caggtgcagc tgcaggagtc tgggggaggc ttggtgcagc ctggggggtc tctgagactc      60
tcctgtacag ctcctcgaat tatttttcttt atgtatgacg tgggctggta tcgccaggct    120
ccagagaagc agcgcgaatt ggtcgcacag attaacagtg atgttagcac gaagtatgca    180
gactccgtga agggccgatt caccatctcc agagacaacg ccaagaggac ggtgtatcta    240
caaatgaacg acctgaaacc tgaggacgcg gccgtgtatt actgtaatgt acggcgagcc    300
tcagccgact attggggcca ggggacccag gtcaccgtct cctca                    345

<210> SEQ ID NO 13
<211> LENGTH: 8
<212> TYPE: PRT
<213> ORGANISM: Vicugna pacos

<400> SEQUENCE: 13

Arg Ile Ile Phe Phe Met Tyr Asp
1               5

<210> SEQ ID NO 14
<211> LENGTH: 24
<212> TYPE: DNA
<213> ORGANISM: Vicugna pacos

<400> SEQUENCE: 14
cgaattattt tctttatgta tgac                                            24

<210> SEQ ID NO 15
<211> LENGTH: 8
<212> TYPE: PRT
<213> ORGANISM: Vicugna pacos

<400> SEQUENCE: 15

Gln Ile Asn Ser Asp Val Ser Thr
1               5

```
<210> SEQ ID NO 16
<211> LENGTH: 24
<212> TYPE: DNA
<213> ORGANISM: Vicugna pacos

<400> SEQUENCE: 16
cagattaaca gtgatgttag cacg                                          24

<210> SEQ ID NO 17
<211> LENGTH: 9
<212> TYPE: PRT
<213> ORGANISM: Vicugna pacos

<400> SEQUENCE: 17

Tyr Cys Asn Val Arg Arg Ala Ser Ala
1               5

<210> SEQ ID NO 18
<211> LENGTH: 27
<212> TYPE: DNA
<213> ORGANISM: Vicugna pacos

<400> SEQUENCE: 18
tactgtaatg tacggcgagc ctcagcc                                       27

<210> SEQ ID NO 19
<211> LENGTH: 7
<212> TYPE: PRT
<213> ORGANISM: Artificial
<220> FEATURE:
<223> OTHER INFORMATION: epitope of second binding polypeptide
<220> FEATURE:
<221> NAME/KEY: MISC_FEATURE
<222> LOCATION: (4)..(4)
<223> OTHER INFORMATION: x = any amino acid
<220> FEATURE:
<221> NAME/KEY: MISC_FEATURE
<222> LOCATION: (7)..(7)
<223> OTHER INFORMATION: x = any amino acid

<400> SEQUENCE: 19

Trp Val Asn Xaa Phe Tyr Xaa
1               5

<210> SEQ ID NO 20
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (6)..(6)
<223> OTHER INFORMATION: y is t or c
<220> FEATURE:
<221> NAME/KEY: misc_feature
<222> LOCATION: (9)..(9)
<223> OTHER INFORMATION: r is g or a

<400> SEQUENCE: 20
atgttyagrt ggatgagatt ctc                                           23

<210> SEQ ID NO 21
<211> LENGTH: 20
<212> TYPE: DNA
<213> ORGANISM: Artificial
<220> FEATURE:
<223> OTHER INFORMATION: PCR primer
```

```
<400> SEQUENCE: 21
tcgacgccat cttcattcac                                           20

<210> SEQ ID NO 22
<211> LENGTH: 20
<212> TYPE: DNA
<213> ORGANISM: Artificial
<220> FEATURE:
<223> OTHER INFORMATION: PCR probe

<400> SEQUENCE: 22
tgggagggcg atcgcaatct                                           20
```

NOROVIRUS ANTIBODIES

CROSS-REFERENCE TO RELATED APPLICATIONS

This application is a U.S. National Phase of International PCT Application No. PCT/EP2018/075324 filed Sep. 19, 2018, which claims priority to European Patent Application Serial No. 17192166.1 filed Sep. 20, 2017, the contents of each application are incorporated herein by reference in their entirety.

The present invention relates to a binding polypeptide specifically binding to an epitope comprised in an amino acid sequence corresponding to amino acids 250 to 300 of the norovirus genotype II.10 capsid polypeptide, and to a polynucleotide encoding the same. The present invention further relates to a composition comprising the binding polypeptide according to the present invention and a carrier, and to the binding polypeptide or the composition comprising the same use in diagnosis and/or for use in medicine. Furthermore, the present invention relates to kits, devices, vaccines, methods, and uses related to the binding polypeptide of the present invention.

Human noroviruses are single-stranded RNA, non-enveloped viruses in the Caliciviridae family and are the most important cause of outbreaks of gastroenteritis. These viruses cannot grow in cell culture, which has hampered vaccine and antiviral development. The genome has three open reading frames (ORF1-3), where ORF1 encodes the non-structural proteins (NS1 to NS7), ORF2 encodes the capsid protein (VP1), and ORF3 encodes a small structural protein. Expression of the capsid protein in insect cells leads to the self-assembly of empty virus-like particles (VLPs) that are morphologically and antigenically similar to native virions (Hansman, G. S., K. Natori, H. Shirato-Horikoshi, S. Ogawa, T. Oka, K. Katayama, T. Tanaka, T. Miyoshi, K. Sakae, S. Kobayashi, M. Shinohara, K. Uchida, N. Sakurai, K. Shinozaki, M. Okada, Y. Seto, K. Kamata, N. Nagata, K. Tanaka, T. Miyamura, and N. Takeda. 2006. Genetic and antigenic diversity among noroviruses. J Gen Virol 87:909-91). Based on the capsid gene sequences, at least five genogroups (GI-GV) have been assigned (Kroneman, A., E. Vega, H. Vennema, J. Vinje, P. A. White, G. Hansman, K. Green, V. Martella, K. Katayama, and M. Koopmans. 2013. Proposal for a unified norovirus nomenclature and genotyping. Arch Virol 158:2059-2068). The genogroups are further subdivided into genotypes and an association between genetic clusters and antigenicity is evident (Hansman et al., loc. cit.).

The X-ray crystal structure of the norovirus GI genotype 1 (GI.1) VLPs showed that VP1 is divided into two domains, shell (S) and protruding (P) (Prasad, B. V., M. E. Hardy, T. Dokland, J. Bella, M. G. Rossmann, and M. K. Estes. 1999. X-ray crystallographic structure of the Norwalk virus capsid. Science 286:287-290). The S domain forms a scaffold surrounding the RNA, whereas the P domain likely contains the determinants for strain diversity. One major structural distinction among these particles is the position of the P domain on the S domain. In the case of GI.1, the P domain is resting on the S domain, whereas in GV.1 and GII.10, the P domains are raised off the S domain by ~15 Å. In most noroviruses, the S and P domains are connected by a flexible hinge region, ~10 amino acids long, which allows for the raised P domains, but likely also permits a certain amount of P domain flexibility on the particles (Smith, T. J. 2011. Structural studies on antibody recognition and neutralization of viruses. Curr Opin Virol 1:150-156).

A variety of anti-norovirus antibodies binding to norovirus capsid proteins has been published, e.g. MAb14-1 418, binding to residues 418 to 426 and 526 to 534 (Shiota T et al., J Virol. 2007 November; 81(22):12298-306); NV23, NS22, and F120, binding to residues 453-472, NS14, binding to residues 473-494, 8C7, binding to residues 451-489 (Crawford S E et al., Clin Vaccine Immunol. 2015 Feb.; 22(2):168-77; Kou B et al., Clin Vaccine Immunol. 2015 Feb.; 22(2):160-7), 5B18, binding to residues 433, 496, 533-535 (Hansman G S et al. J Virol. 2012 April; 86(7): 3635-46), NV3901 and NV3912, binding to residues 454-520 (Parker T D et al., J Virol. 2005 June; 79(12):7402-9), 1B4 and 1F6, binding to residues 45-55 (Yoda T et al., J Clin Microbiol. 2003 June; 41(6):2367-71), N2C3, binding to residues 55-60 (Li X et al., Virus Res. 2009 March; 140(1-2):188-93, Li X et al., Virus Res. 2010 August; 151(2):142-7), an antibody binding residues 52-56 (Gabriel I. Parra et al. PLoS One. 2013; 8(6): e67592), and Nano-85, binding to residues 517-526 (WO 2016/059113).

Nonetheless, little is known about antibody binding epitopes at the structural level. Recently, the first X-ray crystal structure of a norovirus P domain Fab complex was solved (Hansman, G. S., D. W. Taylor, J. S. McLellan, T. J. Smith, I. Georgiev, J. R. Tame, S. Y. Park, M. Yamazaki, F. Gondaira, M. Miki, K. Katayama, K. Murata, and P. D. Kwong. 2012. Structural basis for broad detection of genogroup II noroviruses by a monoclonal antibody that binds to a site occluded in the viral particle. Journal of virology 86:3635-3646; EP2757111 A1). Superposition of the P domain Fab complex on the cryo-EM particle indicated the Fab bound to an occluded site on the particle, i.e., hindered by neighboring P domains. However, this broadly reactive monoclonal antibody recognizes a conserved region on the P domain and is used in a commercial diagnostic ELISA detection kit. Moreover, other monoclonal antibodies are thought to bind this occluded region on particles (Parker et al, loc. cit., Prasad et al. loc. cit.; Shiota et al. loc. cit.). This suggested the occluded region was not only immunoreactive, but also immunodominant.

Despite the described progress toward broadly-reactive antibodies, antibodies suitable in preventing norovirus infection and antibodies permitting broad detection of norovirus strains are still needed. There is, thus, a need in the art for improved antibodies solving the problems as described above.

Problem to be Solved

It is therefore an objective of the present invention to provide improved antibodies avoiding the problems as described above.

SUMMARY OF THE INVENTION

These problems are solved by the binding polypeptides, polynucleotides, methods, kits, devices, and compositions with the features of the independent claims. Typical embodiments, which might be realized in an isolated fashion or in any arbitrary combination are listed in the dependent claims.

Accordingly, the present invention relates to a binding polypeptide specifically binding to an epitope comprised in an amino acid sequence corresponding to amino acids 250 to 300 of the norovirus genotype II.10 capsid polypeptide.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements. It will be understood that any component defined herein as being included may preferably be explicitly excluded from the claimed invention by way of proviso or negative limitation.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

Moreover, if not otherwise indicated, the term "about" relates to the indicated value with the commonly accepted technical precision in the relevant field, preferably relates to the indicated value ±20%, more preferably +10%, most preferably +5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1%, most preferably less than 0.1% by weight of non-specified component(s). In the context of nucleic acid sequences, the term "essentially identical" indicates a % identity value of at least 80%, preferably at least 90%, more preferably at least 98%, most preferably at least 99%. As will be understood, the term essentially identical includes 100% identity. The aforesaid applies to the term "essentially complementary" mutatis mutandis. Unless otherwise noted, nucleic acid sequences and amino acid sequences are noted according to conventional notation, Thus, nucleic acid sequences noted in the direction 5' to 3', and amino acid sequences in the direction N-terminal to C-terminal.

The term "norovirus" is, in principle, known to the skilled person, and relates to a member of the genetically diverse group of non-enveloped, single-stranded RNA viruses of the Caliciviridae family. Preferably, the norovirus is a genogroup GII or GI norovirus. More preferably, the norovirus is a genogroup GII norovirus. Preferably, the norovirus is a GI.1, GII.2, GII.3, GII.5, GII.6, GII.7, or GII.8. More preferably, the norovirus is norovirus GII.1, GII.4, GII.12, GII.17, or GII.10. In accordance, the term "norovirus genotype II.10" relates to a norovirus of genogroup GII, subgroup 10. Preferably, the norovirus genotype II.10 is the norovirus whose genome sequence was submitted under the designation "Norwalk virus strain Vietnam 026" at Genbank, Acc No. AF504671.2.

The term “polypeptide” is known to the skilled person and relates to a chemical compound comprising, preferably consisting of, amino acids chemically bonded by peptide bonds. Preferably, said amino acids are L-amino acids; more preferably are L-amino acids cotranslationally inserted in a polypeptide. The polypeptide may be synthesized chemically, in vitro, or in a biological expression system, in particular a cell.

The term “norovirus genotype II.10 capsid polypeptide”, as used herein, relates to a norovirus capsid polypeptide having the amino acid of Genbank Acc No. AAT12445.1 and SEQ ID NO:1, preferably including sequences essentially identical to the aforesaid sequence. More preferably, the term relates to a norovirus capsid polypeptide having the amino acid of Genbank Acc No. AAT12445.1 and SEQ ID NO:1.

The term “sequence corresponding to amino acids x to y of the norovirus genotype II.10 capsid polypeptide”, preferably, includes sequences from other norovirus strain capsid polypeptides comprising an amino acid sequence corresponding to amino acids x to y of the norovirus genotype II.10 capsid polypeptide, but differing in primary structure from said polypeptide. Thus, included are, preferably, sequences from muteins having the property of being capsid polypeptides. Preferably, the capsid polypeptide variant comprises a peptide having an amino acid sequence corresponding to an amino acid sequence of 50 to 700, more preferably 50 to 500, consecutive amino acids comprised in a norovirus genotype II.10 polypeptide as specified above. Moreover, also encompassed are further polypeptide variants of the aforementioned norovirus genotype II.10 polypeptide. Such polypeptide variants have at least essentially the same biological activity as the specific polypeptides, in particular the activity of assembling into a norovirus capsid under appropriate conditions, in particular in a host cell. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the whole length of the polypeptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to herein may be species or, preferably, strain or substrain specific homologs, paralogs, or orthologs of the norovirus genotype II.10 polypeptide. Moreover, the polypeptide variants referred to herein include fragments of the specific polypeptides or the aforementioned types of polypeptide variants as long as these fragments and/or variants have the properties as referred to above. Such fragments may be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics. More preferably, the sequence corresponding to amino acids x to y of the norovirus genotype II.10 capsid polypeptide is the sequence of the norovirus genotype II.10 capsid polypeptide, preferably as specified herein below.

The term "epitope" is known to the skilled person as a part of an antigen recognized by at least one component of the immune system. According to the present invention, the antigen is a polypeptide, i.e. a norovirus capsid polypeptide, accordingly, the epitope is a continuous or non-continuous stretch of amino acids specifically bound by the binding polypeptide of the invention. More preferably, the epitope is a continuous stretch of from three to 15, more preferably four to 12, most preferably five to tem amino acids. As will be understood, the binding polypeptide of the present invention may additionally bind to one or more further amino acid(s) of its target; thus, the binding polypeptide may further bind to a second epitope. Preferably, the binding of the binding polypeptide to the first and the second epitope occurs via the same binding site on the binding polypeptide in such case.

Preferably, the epitope is comprised in an amino acid sequence corresponding to amino acids 260 to 280, preferably amino acids 269 to 276, of the norovirus capsid polypeptide. Thus, the epitope is preferably comprised in the amino acid sequence YTNPNESAIVQCQNGRCTLD-GELQGTTQLLPTGICAFRGKVTQQVQDEHRG (GII.10 capsid polypeptide fragment 250-300; SEQ ID NO:2). More preferably, the epitope is comprised in the amino acid sequence QCQNGRCTLDGELQGTTQLLP (GII.10 capsid polypeptide fragment 260-280; SEQ ID NO:3). Most preferably, the epitope is comprised in the amino acid sequence DGELQGTT (GII.10 capsid polypeptide fragment 269-276; SEQ ID NO:4). Preferably, the epitope comprises the motif a-x-a-h-x-h-x-o (SEQ ID NO:5), with "x" being any amino acid; "a" being glutamic acid or aspartic acid; "h" being glycine, alanine, valine, leucine or isoleucine, and "o" being serine or threonine. More preferably, the epitope comprises the motif D-x-E-L-x-G-x-T (SEQ ID NO:6), with "x" being any amino acid. Preferably, the binding peptide further specifically binds to a second epitope comprised in the amino acid sequence corresponding to amino acids 450 to 490, preferably amino acids 470 to 488, of said norovirus genotype II.10 capsid polypeptide. Thus, the second epitope is preferably comprised in the amino acid sequence GGYG-NPAIDCLMPQEWVQHLYQESAPSLSDVALVRYVN-PET (GII.10 capsid polypeptide fragment 450-490, SEQ ID NO:7), preferably in the amino acid sequence YQE-SAPSLSDVALVRYVNP (GII.10 capsid polypeptide fragment 470-488, SEQ ID NO:8). Preferably, said second epitope comprises the motif (N or Q)-(D or E), more preferably Q-E. Even more preferably, said second epitope comprises the motif (N or Q)-(D or E)-(x)$_{15}$-P (SEQ ID NO:9), most preferably Y-Q-E-S-x-P-(x)$_{12}$-P (SEQ ID NO:10).

The term, "binding polypeptide", as used herein, relates to a polypeptide specifically binding to an epitope comprised in the amino acid sequence corresponding to amino acids 250 to 300 of a norovirus genotype II.10 capsid polypeptide as specified herein above. Preferably, the binding polypeptide binds to the norovirus polypeptide of the present invention with sufficient affinity to allow detection of a binding polypeptide/norovirus polypeptide complex. Preferably, the dissociation constant (Kd) of the binding polypeptide/norovirus polypeptide complex is at most $10^{-7}$ mol/L, more preferably, at most $10^{-8}$ mol/L, most preferably, at most $10^{-9}$ mol/L. Preferably, the binding polypeptide competes in binding to a capsid polypeptide of a norovirus genogroup II (GII), preferably GII.10, with a VHH comprising the amino acid sequence of SEQ ID NO:11, preferably encoded by SEQ ID NO:12. More preferably, the binding polypeptide comprises the complementarity determining regions (CDRs) RIIFFMYD (CDR1, SEQ ID NO:13), preferably encoded by SEQ ID NO: 14; QINSDVST (CDR2, SEQ ID NO:15), preferably encoded by SEQ ID NO: 16; and YCNVRRASA (CDR3, SEQ ID NO:17), preferably encoded by SEQ ID NO: 18. As will be understood by the skilled person, the relative positioning of the CDRs with regards to each other and to the structural frame can be determined from SEQ ID NO:11.

The term "specifically binding" is understood by the skilled person. Preferably, specific binding relates to a binding in which the affinity of the binding polypeptide to a norovirus capsid polypeptide, preferably a norovirus polypeptide as specified elsewhere herein, is at least tenfold, preferably at least 100fold, most preferably at least 1000fold higher than for any non-target polypeptide or non-norovirus polypeptide present in a sample. Accordingly, the dissociation constant (Kd) of any binding polypeptide/non-target polypeptide complex is at least $10^{-6}$ mol/L, more preferably, at least $10^{-5}$ mol/l, most preferably, at least $10^{-4}$ mol/L.

Preferably, the binding polypeptide of the present invention is an antibody. The term "antibody" is used herein in the broadest sense and specifically covers monoclonal antibodies, polyclonal antibodies, multispecific antibodies (e.g. bispecific antibodies) formed from at least two intact antibodies, single-domain-antibodies (VHH), also known as nanobodies, and antibody fragments so long as they exhibit the desired binding activity as specified elsewhere herein. Preferably, an antibody is not an antibody naturally comprised in an antiserum, typically not a polyclonal antibody or a polyclonal serum. Preferably, the antibody is a full-length antibody or an antibody fragment. More preferably, the antibody is a monoclonal antibody. Most preferably, the antibody is a VHH (nanobody).

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

"Antibody fragments" comprise a portion of an intact antibody, in an embodiment, comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. Preferably, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs, also referred to as complementarity determining regions (CDRs)) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "monoclonal antibody" as used herein refers to an antibody obtained from a population of essentially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Preferably, such a monoclonal antibody includes an antibody comprising a polypeptide sequence that binds a norovirus polypeptide, wherein the target-binding polypeptide sequence was obtained by a process that includes the selection of a single binding polypeptide sequence from a plurality of polypeptide sequences. For example, the selection process can be the selection of a unique clone from a plurality of clones, such as a pool of hybridoma clones, phage clones, or recombinant DNA clones.

The term "single-domain antibody" (VHH) or "nanobody", relates to an antibody fragment comprising one variable antibody domain and is, in principle, known to the skilled person. A review is provided, e.g. in Muyldermanns et al. (2009), Vet Immunol Immunopathol. 128(1-3):178. Preferably, the VHH comprises the CDRs of a heavy-chain antibody, preferably obtained from an alpaca, dromedar, camel, llama, or shark immunized with a target polypeptide. More preferably, the VHH has the binding properties as specified above. Still more preferably, the VHH comprises the complementarity determining regions (CDRs) RIIFF-MYD (CDR1, SEQ ID NO:13), preferably encoded by SEQ ID NO: 14; QINSDVST (CDR2, SEQ ID NO:15), preferably encoded by SEQ ID NO: 16; and YCNVRRASA (CDR3, SEQ ID NO:17), preferably encoded by SEQ ID NO: 18. Most preferably, the VHH comprises the amino acid sequence of SEQ ID NO:11, preferably encoded by a polynucleotide comprising the nucleic acid sequence of SEQ ID NO: 12.

It is understood by the skilled person that the binding properties of an antibody, in particular of a VHH, usually are conserved if amino acids, in particular those not comprised in a CDR, are exchanged. Accordingly, the term binding polypeptide also relates to polypeptides comprising an amino acid sequence having at least 70%, more preferably at least 80%, still more preferably at least 90%, even more preferably at least 95%, most preferably at least 99%, sequence identity to SEQ ID NO:11 and having the property of specifically binding the norovirus polypeptide according to the present invention. More preferably, term binding polypeptide also relates to polypeptides comprising an amino acid sequence having at least 70% sequence identity to SEQ ID NO:11 and comprising CDR1, CDR2, and/or CDR3 as specified above, preferably located within the sequence at essentially the same position(s) as in SEQ ID NO:11. Such exchanges of amino acids and variants can e.g. be used for providing a humanized binding polypeptide or a binding polypeptide resistant to acid or enzymatic cleavage.

Also, preferably, the binding polypeptide may be, preferably covalently, linked to a chemical molecule. Methods how to covalently link a polypeptide with a chemical molecule are known in the art. Preferred chemical molecules for covalently linking with the binding polypeptide of the present invention are polymers like, e.g. polyethylene glycol, polysaccharides such as starch or one of its derivatives, targeting molecules, and the like.

Moreover, the binding polypeptide may be a fusion polypeptide comprising a further polypeptide portion with a further functionality. E.g. said fusion polypeptide may comprise a linker and/or a tag. As used herein, the term "tag" relates to a detectable chemical or physical moiety covalently connected with the binding polypeptide of the present invention. In an aspect, the tag is an affinity tag or, preferably, a hapten, i.e. a tag having affinity to an affinity compound. In yet a further aspect, the binding of the affinity tag to the affinity compound has a dissociation constant so low that the affinity tag will only dissociate to a negligible extent from the affinity compound. In a yet further aspect, the dissociation constant of the affinity tag:affinity compound pair is less than $10^{-5}$ mol/l (as it is the case with the Strep-Tag:Strep-Tactin binding), less than $10^{-6}$ mol/l (as it is the case in the Strep-TagII:Strep-Tactin binding), less than $10^{-7}$ mol/l (as it is typically the case in antibody:antigen binding), less than $10^{-8}$ mol/l, less than $10^{-10}$ mol/l, or less than $10^{-12}$ mol/l (as it is the case for the Streptavidin:Biotin binding). E.g., preferably, hapten-conjugated nanobodies may be used for the detection of bound norovirus polypeptide or nanovirus particles, preferably in combination with specific conjugates like peroxidase labeled streptavidin. Methods of determining dissociation constants are well known to the skilled artisan and include, e.g., spectroscopic titration methods, surface plasmon resonance measurements, equilibrium dialysis and the like. Preferably, the affinity tag is a His-tag, Strep-tag, V5-tag, Myc-tag, HA-tag, FLAG-tag, or GST. More preferably, the tag is an enzymatic marker tag, i.e. a tag having an enzymatic activity determinable under appropriate conditions. Suitable enzymatic marker tags are well known in the art and include, e.g. horseradish peroxidase, alkaline phosphatase, luciferase, or beta-galactosidase, and the like. In another aspect, the term tag relates to a fluorescent protein tag. Fluorescent protein tags are well known in the art and include the fluorescent proteins from various organisms, e.g. *Aequorea victoria, Verrillofungia concinna, Lobophyllia hemprichii, Goniastrea australensis, Favia favus*, and the like, as well as derivatives having a wildtype or a modified excitation- and/or emission-spectrum, like GFP, eGFP, YFP, CFP, or RFP. It is understood by the skilled person that a tag of the present invention is not necessarily restricted to one of the categories as detailed above; e.g. an enzymatic marker tag or a fluorescent protein tag may also be used as an affinity tag, e.g. by using an appropriate antibody recognizing said enzymatic marker tag or fluorescent protein tag. Preferably, the tag is genetically encoded, i.e. the tag is provided as the encoding polynucleotide.

Methods for determining the amount of a fusion polypeptide comprising a tag as described herein are well known in the art and depend on the kind of tag used. In a preferred embodiment, a hapten may be used to either coat a solid phase like magnetic particles or microtiter plates. Preferably, the amount of a tagged cleavage product comprising an enzymatic marker tag is determined by incubating a sample comprising said enzymatic marker tag with an appropriate substrate, the product of which produced by the enzymatic action of said enzymatic marker tag can be determined. Examples of substrate/enzymatic marker pairs include 3,3', 5,5'-Tetramethylbenzidine (TMB), 3,3'-Diaminobenzidine (DAB), or 2,2'-Azino-bis(3-ethylbenzothiazoline-6-sulphonic acid) (ABTS) conversion by horseradish peroxidase; 4-Methylumbelliferyl phosphate (4-MUP) or p-Nitrophenyl phosphate conversion by alkaline phosphatase; luciferin conversion by luciferase; or 5-Bromo-4-chloro-indolyl-3-D-galactopyranoside conversion by beta-galactosidase. Also preferably, the amount of a tag comprising a fluorescent protein tag is determined by illuminating said fluorescent protein tag at an appropriate wavelength and determining absorbance or fluorescence of the tag. It is understood by the skilled person that practically any tag can be determined by immunological methods, provided that a specific antibody for said tag is available or can be generated.

Advantageously, it was found in the work underlying the present invention that the binding polypeptide of the present invention has the capacity of broadly recognizing members of the genus norovirus. Accordingly, such an antibody can be used in diagnostic tests screening broadly for norovirus infection. Moreover, said antibody has the potential to be used for inhibiting norovirus infection without the need to know which genotype. Moreover, it was found that the antibody of the present invention can inactivate norovirus particles by binding to the specific site indicated, and thereby prevent further spread of an infection. Advantageously, it is also envisaged to use the binding polypeptide of the present invention for sanitization and disinfection purposes. Also, since nanobodies are easy and cost-effective to produce, this offers the possibility to provide norovirus detection kits at low cost. Moreover, since nanobodies are small and can be applied at high densities onto solid surfaces, the sensitivity of norovirus-assays can be improved. The small size of nanobodies is, preferably, particularly advantageous e.g. in immuno-chromatography, since it allows for applying a high molar concentration of antibody onto a limited space; therefore, preferably, a combination of several nanobodies may be used to increase the range of detectable genotypes while not compromising sensitivity. Furthermore, it was found that the antibody of the present invention synergizes with the antibody of WO 2016/059113 in disassembling norovirus capsids.

The definitions made above apply mutatis mutandis to the following. Additional definitions and explanations made further below also apply for all embodiments described in this specification mutatis mutandis.

The present invention further relates to a polynucleotide encoding a binding polypeptide according to the present invention, preferably a polynucleotide which (i) encodes a binding polypeptide comprising an amino acid sequence of SEQ ID NO:11, (ii) comprises a nucleotide sequence as shown in SEQ ID NO:12, (iii) encodes a binding polypeptide comprising an amino acid sequence having at least 70% sequence identity to SEQ ID NO:11, or/and (iv) comprises a nucleotide sequence having at least 70% sequence identity to a nucleotide sequence as shown in SEQ ID NO:12.

The term "polynucleotide", as used in accordance with the present invention, relates to a polynucleotide comprising a nucleic acid sequence which encodes a polypeptide having the biological property of specifically binding to a norovirus polypeptide as specified herein above. Suitable assays for measuring the activities mentioned before are described in the accompanying Examples or in standard literature. A polynucleotide encoding a polypeptide having the aforementioned biological activity has been obtained in accordance with the present invention from an alpaca. The polynucleotide, preferably, comprises the nucleic acid sequence shown in SEQ ID NO:12 encoding the polypeptide having an amino acid sequence as shown in SEQ ID NO:11. It is to be understood that a polypeptide having an amino acid sequence as shown in SEQ ID NO:11 may be also encoded, due to the degenerated genetic code, by other polynucleotides as well. It is also understood that, depending on the specific expression system selected, adaptation of codon usage may improve yields.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences shown in SEQ ID NO:12 by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker from standard text books. A preferred example for stringent hybridization conditions are hybridization conditions in 6' sodium chloride/sodium citrate (=SSC) at approximately 45° C., followed by one or more wash steps in 0.2' SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5' SSC (pH 7.2). If organic solvent is present in the abovementioned buffer, for example 50% formamide, the temperature under standard conditions is approximately 42° C. The hybridization conditions for DNA:DNA hybrids are preferably for example 0.1' SSC and 20° C. to 45° C., preferably between 30° C. and 45° C. The hybridization conditions for DNA:RNA hybrids are preferably, for example, 0.1' SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to standard textbooks of molecular biology. Further, variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO:12. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO:11. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has the activity as specified above. Accordingly, the polypeptide encoded may comprise or consist of the domains of the polypeptide of the present invention conferring the said biological activity. A fragment as meant herein, preferably, comprises at least 60, at least 75, at least 90 or at least 120 consecutive nucleotides of any one of the aforementioned nucleic acid sequences or encodes an amino acid sequence comprising at least 20, at least 25, at least 30, or at least 40 consecutive amino acids of any one of the aforementioned amino acid sequences.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. isolated from its natural context) or in genetically modified form. The polynucleotide, preferably, is DNA, including cDNA, or RNA. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides.

The present invention also relates to a host cell comprising the binding polypeptide according to the present invention or the polynucleotide according to the present invention.

The term "host cell", as used herein, relates to a an eukaryotic or, preferably, prokaryotic cell. Preferably, the cell is a cultured cell of a mammal, more preferably a human cell. More preferably, the cell is a bacterial or fungal cell, still more preferably an *Escherichia coli* cell.

The present invention further relates to a composition comprising the binding polypeptide according to any the present invention and a carrier.

The term "composition", as used herein, relates to a mixture of compounds comprising at least the binding polypeptide of the present invention and at least one carrier. The carrier(s) must be acceptable in the sense of being compatible with the other ingredients of the composition and being not deleterious to a potential recipient thereof. The carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa. The carrier(s) is/are selected so as not to affect the biological activity of the composition. Examples of such diluents are distilled water, physiological saline, Ringer's solutions, dextrose solution, and Hank's solution.

Preferably, the composition is a disinfectant. Thus preferably, the composition is used for inactivating norovirus which may be comprised in a solution or, preferably, on a surface. Preferably, said surface is a body surface, preferably of a subject infected with a norovirus or a subject in contact with such an infected subject. As will be understood, the composition may comprise additional components with disinfectant properties in such case, such as one or more alcohol(s). Preferably, the composition further comprises at least one of a protease and an RNase. Also preferably, the composition further comprises at least one of a detergent and a disinfectant. More preferably, the composition further comprises at least a second binding polypeptide specifically binding to a further epitope comprised in the amino acid sequence of a norovirus capsid polypeptide, more preferably wherein said further epitope is non-identical to the epitope and second epitope as detailed above, and is non-identical to an epitope recognized by the binding polypeptide of the present invention. Even more preferably, the second binding polypeptide specifically binds to the amino acid sequence W-V-N-x-F-Y-x, with x being any amino acid (SEQ ID NO:19). Most preferably, the second binding polypeptide is the binding polypeptide of WO 2016/059113, which is herewith incorporated by reference; in particular is the nanobody nano-85 disclosed therein.

Preferably, the composition is a pharmaceutical composition; thus, preferably, the carrier is a pharmaceutically acceptable carrier. In addition, the pharmaceutical composition or formulation may also include other carriers, adjuvants, or nontoxic, nontherapeutic, nonimmunogenic stabilizers and the like. The binding polypeptide of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. Preferably, administration is peroral. However, depending on the nature and mode of action of a compound, the pharmaceutical compositions may be administered by other routes as well. Moreover, the binding polypeptide can be administered in combination with other drugs either in a common pharmaceutical composition or as separated pharmaceutical compositions wherein said separated pharmaceutical compositions may be provided in form of a kit of parts. The binding polypeptide is, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. Preferably, in case of peroral administration, a preparation comprising an acid-resistant coating is used.

A therapeutically effective dose refers to an amount of the binding polypeptide to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 1 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The present invention also relates to a binding polypeptide according to the present invention or a composition according to the present invention for use in diagnosis; and/or for use in diagnosing a norovirus-infection in a sample of a subject.

The term "diagnosing", as used herein, refers to assessing the probability according to which a subject is suffering or will suffer from a disease or condition referred to in this specification, in particular norovirus infection. As will be understood by those skilled in the art, such an assessment is usually not intended to be correct for 100% of the subjects to be diagnosed. Preferably, the term requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population.

The term "subject" as referred to herein encompasses animals which can be infected by a norovirus, preferably mammals, and, more preferably, humans. More preferably, said subject suffers from, is suspected to suffer from, or is at risk to suffer from a norovirus infection. It will be understood that said term, preferably, includes subjects suspected to be asymptomatic norovirus carriers. Subjects which suffer from the said infection can be identified by the accompanying symptoms known for the disease. These symptoms are known in the art and described, e.g., in standard text books of medicine. A subject suspected to suffer from the aforementioned disease may be any apparently healthy subject, e.g., investigated by routine clinical screening, or may be a subject being at risk for developing the aforementioned disease.

The present invention also relates to a binding polypeptide according to the present invention or a composition according to the present invention for use in medicine, and/or for use in treating and/or preventing a norovirus-infection in a subject.

The term "treating" refers to ameliorating the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well known statistic evaluation tools as described herein above.

The tem "preventing" refers to retaining health with respect to the diseases or disorders referred to herein for a certain period of time in a subject. It will be understood that the said period of time is dependent on the amount of the binding polypeptide which has been administered and individual factors of the subject discussed elsewhere in this specification. It is to be understood that prevention may not be effective in all subjects treated with the compound according to the present invention. However, the tem requires that, preferably, a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed elsewhere in this specification.

The present invention further relates to the use of the binding polypeptide according to the present invention or a composition according to the present invention for diagnosing, treating and/or preventing a norovirus-infection. Moreover, the present invention relates to use of the binding polypeptide according to the present invention for inactivating a norovirus particle.

As used herein, the term "inactivating a norovirus particle" relates to inducing a, preferably irreversible, change in the structure and/or composition of the norovirus particle causing the norovirus particle to become non-infectious and/or replication incompetent. Preferably, inactivating is preventing the norovirus particle from binding to its cognate receptor, preventing the norovirus particle from unpacking its genome, or destroying the structure of the norovirus particle.

The present invention further relates to a method of detecting the presence of a norovirus capsid polypeptide in a sample, comprising
(a) contacting said sample to the binding polypeptide according to the present invention or a composition according to the present invention,
(b) detecting the amount of binding polypeptide/norovirus capsid polypeptide complexes in said sample, thereby
(c) detecting the presence of norovirus capsid polypeptides in said sample.

The method of detecting the presence of a norovirus capsid polypeptide of the present invention, preferably, is an in vitro method. Moreover, it may comprise steps in addition to those explicitly mentioned above. For example, further steps may relate, e.g., to taking or providing a sample for step a), or contacting the binding polypeptide/norovirus capsid polypeptide complexes from step b) to a detection agent. Moreover, one or more of said steps may be performed by automated equipment. Also, preferably, detecting the presence of a norovirus capsid polypeptide is detecting the presence of norovirus particles. Accordingly, detecting the presence of a norovirus capsid polypeptide in a sample from a subject, preferably, is indicative of a norovirus infection prevalent in said subject. Thus, the method of detecting the presence of a norovirus capsid polypeptide, preferably, is a method of diagnosing a norovirus infection.

The term "sample", as used herein, refers to any sample suspected or known to comprise a norovirus capsid polypeptide. It envisaged according to the present invention that the sample may be, e.g. a food sample, a swab from a surface in a kitchen, or a sample of cell culture supernatant. Preferably, however, the sample is a sample of a body fluid, a sample of separated cells, a sample from a tissue or an organ, or a sample of wash/rinse fluid obtained from an outer or inner body surface of a subject. More preferably, the sample is body fluids like blood, plasma, serum, urine, saliva, or lacrimal fluid. Most preferably, the sample is a stool sample. Samples can be obtained by well known techniques and include, preferably, scrapes, swabs or biopsies. Such samples can be obtained by use of brushes, (cotton) swabs, spatula, rinse/wash fluids, punch biopsy devices, puncture of cavities with needles or surgical instrumentation. Preferably, the sample originates from blood or liver. More preferably, the sample originates from the urogenital tract, the oral cavity, the upper aerodigestive tract and the epidermis. Most preferably, the sample originates from the anal canal. Separated cells and/or cell-free liquids may be obtained from cell culture supernatants, body fluids, or the tissues or organs by separating techniques such as filtration, centrifugation, or cell sorting. Separated cells, preferably, are lysed before being used as samples in the present invention by one of the methods well known to the skilled artisan. It is to be understood that the sample may be further processed in order to carry out the method of the present invention. Preferably, in the method for detecting the presence of a norovirus capsid polypeptide, the sample is a sample suspected to comprise norovirus of at least one of genogroup GI and GII, preferably at least one of GI.1, GI.11, GII.1, GII.2, GII.4 2006, GII.4 2012, GII.10, GII.12, and GII.17.

The term "contacting" as used in the context of the methods of the present invention is understood by the skilled person. Preferably, the term relates to bringing a binding polypeptide of the present invention in physical contact with a sample and thereby, e.g. allowing the sample and the binding polypeptide to interact. Preferably, contacting is performed under conditions allowing stable interaction between a binding polypeptide and a norovirus polypeptide.

The amount of binding polypeptide/norovirus capsid polypeptide can be determined in a sample of a subject by techniques well known in the art, including those described herein above. Depending on the nature of the sample, the amount may be determined by ELISA based techniques or by an immuno-chromatography method. To this end, antibodies or aptamers may be used as detection agents which specifically bind to at least one component of the binding polypeptide/norovirus capsid polypeptide and which, upon binding, can be detected by a detectable label. How such antibodies or aptamers can be generated is known to the skilled person. A detectable label may be covalently or reversibly linked to the antibody or aptamer. A covalently linked label may be a radioactive, fluorophore or chemiluminescent moiety while a reversible label may be a secondary antibody or an aptamer which specifically binds to the detection agent and which upon binding can be used to detect the bound detection agent.

The present invention also relates to a method of treating a norovirus infection in a subject, comprising
(a) contacting said subject to a binding polypeptide according to the present invention or a composition according to the present invention, thereby
(b) treating said norovirus infection in said subject.

The method of treating a norovirus infection of the present invention, preferably, is an in vivo method. Moreover, it may comprise steps in addition to those explicitly mentioned above. For example, further steps may relate, e.g., to diagnosing a norovirus infection, preferably according to the method of detecting the presence of a norovirus capsid polypeptide of the present invention before step a), or administering a further pharmaceutically active compound to said subject. Moreover, one or more of said steps may be performed by automated equipment.

Contacting a subject with the binding polypeptide of the present invention, preferably, is administering said binding polypeptide comprised in a composition, preferably a pharmaceutical composition, more preferably as specified herein above.

The present invention also relates to a method of preventing a norovirus infection, comprising
(a) contacting an object suspected to comprise a norovirus particle with a binding polypeptide according to the present invention or a composition according to the present invention, thereby
(b) preventing a norovirus infection.

The method of preventing a norovirus infection of the present invention, preferably, is an in vitro method; It may, however, also be performed in vivo, e.g. by prophylactically administering the binding polypeptide of the present invention to a subject. Moreover, it may comprise steps in addition to those explicitly mentioned above. For example, further steps may relate, e.g., to estimating the risk of a subject of becoming infected by a norovirus before step a), or applying further chemical compounds, e.g. disinfectants, to an object. Moreover, one or more of said steps may be performed by automated equipment.

For the method of preventing a norovirus infection by contacting a subject at risk of becoming infected, the definitions provided for the method of treating a norovirus infection in a subject provided herein above apply mutatis mutandis. As will be understood by the skilled person, preventing in such case may also include treating the skin of the hands with the binding polypeptide of the present invention.

For the method of preventing a norovirus infection by contacting object suspected to comprise a norovirus particle, it is envisaged that the binding polypeptide of the present invention is applied to said object in order to inactivate viral particles potentially comprised on its surface or therein. Accordingly, the term "object", as used herein, relates to any physical object suspected to comprise norovirus particles. Preferably, said object is a part of the equipment of a lavatory, e.g. a toilet seat, a toilet bowl, a basin, or a faucet. It is, however, also envisaged that the object is an object in another area at high risk of norovirus spread, e.g. equipment and surfaces in a canteen kitchen.

Further, the present invention relates to a kit for diagnosing, preventing or/and treating a norovirus infection, comprising the binding polypeptide according to the present invention in a housing.

The term "kit" as used herein refers to a collection of the aforementioned means, e.g., a composition comprising the binding polypeptide of the current invention and/or means for contacting a sample under conditions which allow for forming complexes between said binding polypeptide and a norovirus polypeptide, preferably, provided separately or within a single container. The container, also preferably, comprises instructions for carrying out the method of the present invention. The components of the kit are provided, preferably, in a "ready-to-use" manner, e.g., concentrations are adjusted accordingly, etc. Preferably, the kit further comprises at least a second binding polypeptide specifically binding to a second epitope comprised in the amino acid sequence a norovirus capsid polypeptide, preferably wherein said second epitope is non-identical to the epitope or an epitope recognized by said binding polypeptide. More preferably, the second binding polypeptide specifically binds to the amino acid sequence W-V-N-x-F-Y-x (SEQ ID NO:19) as specified herein above. Also preferably, the kit further comprises at least one of a protease and an RNase, further comprises a pharmaceutically acceptable carrier, and/or further comprises at least one of a detergent and a disinfectant.

Also, the present invention relates to a device for diagnosing a norovirus infection, comprising the binding polypeptide according to the present invention and means for determining the amount binding polypeptide/norovirus polypeptide complexes formed in the presence of a sample.

The term "device" as used herein in the context of a device for diagnosing a norovirus infection relates to a system of means comprising at least the means operatively linked to each other as to allow the diagnosis. Preferred means for determining the amount of binding polypeptide/norovirus polypeptide formed in the presence of a sample are well known in the art. How to link the means in an operating manner will depend on the type of means included into the device. Preferably, the means are comprised by a single device in such a case. Said device may accordingly include a detection unit and a computer unit for processing data obtained from the detection unit for determining the amount of binding polypeptide/norovirus polypeptide complex. However, it is also contemplated that the means of the current invention may appear as separate devices in such an embodiment and are, preferably, packaged together as a kit. The person skilled in the art will realize how to link the means without further ado. Preferred devices are those which can be applied without the particular knowledge of a specialized technician.

The present inventions further relates to a device for preventing or/and treating a norovirus infection, comprising the binding polypeptide according to the present invention and means for administering the same.

The term "device", as used herein in the context of a device for preventing or/and treating a norovirus infection, relates to a system of means comprising at least the means operatively linked to each other as to allow administration of the compound or of the medicament of the present invention. Preferred means for administering medicaments are well known in the art. How to link the means in an operating manner will depend on the type of means included into the device and on the kind of administration envisaged. Preferably, the means are comprised by a single device in such a case. Said device may accordingly include a delivery unit for the administration of the compound or medicament and a storage unit for storing said compound or medicament until administration. However, it is also contemplated that the means of the current invention may appear as separate devices in such an embodiment and are, preferably, packaged together as a kit. The person skilled in the art will realize how to link the means without further ado. Preferred devices are those which can be applied without the particular knowledge of a specialized technician. In a preferred embodiment, the device is a syringe, more preferably with a needle, comprising the compound or medicament of the invention. In another preferred embodiment, the device is an intravenous infusion (IV) equipment comprising the compound or medicament. In another preferred embodiment, the device is an endoscopic device comprising the compound or medicament for flushing a site of norovirus infection. In still another preferred embodiment the device is an inhaler comprising the compound of the present invention, wherein, more preferably, said compound is formulated for administration as an aerosol.

Moreover, the present invention relates to a vaccine comprising a peptide comprising an epitope comprised in an amino acid sequence corresponding to amino acids 250 to 300 of the norovirus genotype II.10 capsid polypeptide.

Preferably, the epitope is comprised in the amino acid sequence corresponding to amino acids 260 to 280, preferably 269 to 276, of the norovirus genotype II.10 capsid polypeptide, as specified herein above. Also preferably, the epitope comprises the motif a-x-a-h-x-h-x-o (SEQ ID NO:5), with "x" being any amino acid; "a" being glutamic acid or aspartic acid; "h" being glycine, alanine, valine, leucine or isoleucine, and "o" being serine or threonine; more preferably, the epitope comprises the motif D-x-E-L-x-G-x-T (SEQ ID NO:6). Preferably, the vaccine consists of at most 100, preferably at most 50, more preferably at most 25 amino acids.

In view of the above, the following embodiments are preferred:

1. A binding polypeptide specifically binding to an epitope comprised in an amino acid sequence corresponding to amino acids 250 to 300 of the norovirus genotype II.10 capsid polypeptide.

2. The binding polypeptide of embodiment 1, wherein said epitope is comprised in the amino acid sequence corresponding to amino acids 260 to 280, preferably amino acids 269 to 276, of said norovirus capsid polypeptide.

3. The binding polypeptide of embodiment 1 or 2, wherein said epitope comprises the motif a-x-a-h-x-h-x-o (SEQ ID NO:5), with "x" being any amino acid; "a" being glutamic acid or aspartic acid; "h" being glycine, alanine, valine, leucine or isoleucine, and "o" being serine or threonine.

4. The binding polypeptide of any one of embodiments 1 to 3, wherein said epitope comprises the motif D-x-E-L-x-G-x-T (SEQ ID NO:6).

5. The binding polypeptide of any one of embodiments 1 to 4, wherein said binding peptide further specifically binds to a second epitope comprised in the amino acid sequence corresponding to amino acids 450 to 490, preferably amino acids 470 to 488, of said norovirus genotype II.10 capsid polypeptide.

6. The binding polypeptide of embodiment 5, wherein said second epitope comprises the motif N or Q-D or E, preferably Q-E.

7. The binding polypeptide of embodiment 5 or 6, wherein said motif second epitope comprises the motif N or Q-D or E-(x)$_{15}$-P, preferably Y-Q-E-S-x-P-(x)$_{12}$-P (SEQ ID NO:10).

8. The binding polypeptide of any one of embodiments 1 to 7, wherein said binding polypeptide is an antibody.

9. The binding polypeptide of any one of embodiments 1 to 8, wherein said binding polypeptide is an antibody fragment.

10. The binding polypeptide of any one of embodiments 1 to 9, wherein said binding polypeptide is an Fab fragment, an Fab' fragment, an Fv fragment, a single-chain Fv antibody, or a single-domain antibody (VHH).

11. The binding polypeptide of any one of embodiments 1 to 10, wherein said binding polypeptide is a single-domain antibody (VHH).

12. The binding polypeptide of any one of embodiments 1 to 11, wherein said binding polypeptide competes in binding to a capsid polypeptide of a norovirus genogroup II (GII) with a VHH comprising the amino acid sequence of SEQ ID NO:11, preferably encoded by SEQ ID NO:12.

13. The binding polypeptide of any one of embodiments 1 to 12, wherein said binding polypeptide comprises the complementarity determining regions (CDRs) of SEQ ID NOs:13, 15, and 17.

14. The binding polypeptide of any one of embodiments 1 to 13, wherein said binding polypeptide comprises an amino acid sequence essentially having the amino acid sequence of SEQ ID NO:11; preferably wherein said binding polypeptide comprises an amino acid sequence having the amino acid sequence of SEQ ID NO:11 or comprises an amino acid sequence having at least 70% sequence identity to SEQ ID NO: 11.

15. A polynucleotide encoding a binding polypeptide according to any one of embodiments 1 to 14.

16. The polynucleotide of embodiment 15, wherein said polynucleotide
(i) encodes a binding polypeptide comprising an amino acid sequence of SEQ ID NO:11,
(ii) comprises a nucleotide sequence as shown in SEQ ID NO:12,
(iii) encodes a binding polypeptide comprising an amino acid sequence having at least 70% sequence identity to SEQ ID NO:11, or/and
(iv) comprises a nucleotide sequence having at least 70% sequence identity to a nucleotide sequence as shown in SEQ ID NO:12.

17. A host cell comprising the binding polypeptide according to any one of embodiments 1 to 14 or the polynucleotide according to embodiment 15 or 16.

18. A composition comprising the binding polypeptide according to any one of embodiments 1 to 14 and a carrier.

19. The composition of embodiment 18, wherein said composition further comprises at least a second binding polypeptide specifically binding to a second epitope comprised in the amino acid sequence of a norovirus capsid polypeptide, preferably wherein said second epitope is non-identical to the epitope or an epitope recognized by said binding polypeptide.

20. The composition of embodiment 18 or 19, wherein said second binding polypeptide specifically binds to the amino acid sequence W-V-N-x-F-Y-x (SEQ ID NO:19).

21. The composition of any one of embodiments 18 to 20, wherein said composition further comprises at least one of a protease and an RNase.

22. The composition of any one of embodiments 18 to 21, wherein said carrier is a pharmaceutically acceptable carrier.

23. The composition of any one of embodiments 18 to 22, wherein said composition further comprises at least one of a detergent and a disinfectant.

24. A binding polypeptide according to any one of embodiments 1 to 14 or a composition according to any one of embodiments 18 to 23 for use in diagnosis.

25. A binding polypeptide according to any one of embodiments 1 to 14 or a composition according to any one of embodiments 18 to 23 for use in diagnosing a norovirus-infection in a sample of a subject.

26. A binding polypeptide according to any one of embodiments 1 to 14 or a composition according to any one of embodiments 18 to 23 for use in medicine.

27. A binding polypeptide according to any one of embodiments 1 to 14 or a composition according to any one of embodiments 18 to 23 for use in treating and/or preventing a norovirus-infection in a subject.

28. Use of the binding polypeptide according to any one of embodiments 1 to 14 or a composition according to any one of embodiments 18 to 23 for diagnosing, treating and/or preventing a norovirus-infection.

29. Use of the binding polypeptide according to any one of embodiments 1 to 14 or a composition according to any one of embodiments 18 to 23 for inactivating a norovirus particle.

30. A method of detecting the presence of a norovirus capsid polypeptide in a sample, comprising
(a) contacting said sample to the binding polypeptide according to any one of embodiments 1 to 14 or a composition according to any one of embodiments 18 to 23,
(b) detecting the amount of binding polypeptide/norovirus capsid polypeptide complexes in said sample, thereby
(c) detecting the presence of norovirus capsid polypeptides in said sample.

31. The method of embodiment 30, wherein said sample is a sample of a subject.

32. A method of treating a norovirus infection in a subject, comprising
(a) contacting said subject to a binding polypeptide according to any one of embodiments 1 to 14 or a composition according to any one of embodiments 18 to 22, thereby
(b) treating said norovirus infection in said subject.

33. A method of preventing a norovirus infection, comprising
(a) contacting an object suspected to comprise a norovirus particle with a binding polypeptide according to any one of embodiments 1 to 14 or a composition according to any one of embodiments 18 to 23, thereby
(b) preventing a norovirus infection.

34. Use of a binding polypeptide according to any one of embodiments 1 to 14 or a composition according to any one of embodiments 18 to 23 for the manufacture of a diagnostic compound, kit, or device for diagnosing a norovirus infection.

35. Use of a binding polypeptide according to any one of embodiments 1 to 14 for the manufacture of a therapeutic composition, kit, or device for the treatment of a norovirus infection.

36. A kit for diagnosing, preventing or/and treating a norovirus infection, comprising the binding polypeptide of any one of embodiments 1 to 14 in a housing.

37. The kit of embodiment 36, wherein said kit further comprises at least a second binding polypeptide specifically binding to a second epitope comprised in the amino acid sequence a norovirus capsid polypeptide, preferably wherein said second epitope is non-identical to the epitope or an epitope recognized by said binding polypeptide.

38. The kit of embodiment 36 or 37, wherein said second binding polypeptide specifically binds to the amino acid sequence W-V-N-x-F-Y-x (SEQ ID NO:19).

39. The kit of any one of embodiments 36 to 38, wherein said kit further comprises at least one of a protease and an RNase.

40. The kit of any one of embodiments 36 to 39, wherein said kit further comprises a pharmaceutically acceptable carrier.

41. The kit of any one of embodiments 36 to 40, wherein said kit further comprises at least one of a detergent and a disinfectant.

42 A device for diagnosing a norovirus infection, comprising the binding polypeptide of any one of embodiments 1 to 14 and means for determining the amount binding polypeptide/norovirus polypeptide complexes formed in the presence of a sample.

43. A device for preventing or/and treating a norovirus infection, comprising the binding polypeptide of any one of embodiments 1 to 14 and means for administering the same.

44. A vaccine comprising a peptide comprising an epitope comprised in an amino acid sequence corresponding to amino acids 250 to 300 of the norovirus genotype II.10 capsid polypeptide.

45. The vaccine of embodiment 44, wherein said epitope is comprised in the amino acid sequence corresponding to amino acids 260 to 280, preferably 269 to 276, of the norovirus genotype II.4 capsid polypeptide.

46. The vaccine of embodiment 44 or 45, wherein said epitope comprises the motif a-x-a-h-x-h-x-o (SEQ ID NO:5), with "x" being any amino acid; "a" being glutamic acid or aspartic acid; "h" being glycine, alanine, valine, leucine or isoleucine, and "o" being serine or threonine.

47. The vaccine of any one of embodiments 44 to 46, wherein said epitope comprises the motif D-x-E-L-x-G-x-T (SEQ ID NO:6).

48. The vaccine of any one of embodiments 44 to 47, wherein said vaccine consists of at most 100, preferably at most 50, more preferably at most 25 amino acids.

All references cited in this specification are herewith incorporated by reference with respect to their entire disclosure content and the disclosure content specifically mentioned in this specification.

FIGURE LEGENDS

FIG. 1. Nano-26 cross-reactivites and inhibition of GII.10 VLP attachment to PGM and saliva. Nanobody cross-reactivities were analyzed using a panel of GII and GI noroviruses in direct ELISA. P domains, 15 µg/ml, (GII.1, GII.2, GII.4, GII.10, GII.12, GII.17) or VLPs, 4 µg/ml, (GI.1 and GI.11) were detected with a panel of serially diluted Nanobody Nano-26. Nano-26 recognized GII.1, GII.2, GII.4, GII.10, GII.12, and GII.17 P domains. All experiments were performed in triplicate (error bars are shown) and the cutoff was set at an OD490 of 0.15 (dashed line). (B) PGM blocking assay was used as a surrogate neutralization assay. GII.10 VLPs were pretreated with serially diluted Nano-26 and added on PGM coated plates. For Nano-26, the IC50 value was 6.6 µg/ml. (C-D) Saliva blocking assay with GII.10 VLPs (2.5 µg/ml) was performed similarly to PGM binding assay with saliva type A (C) or type B (D). Nano-26 inhibited 50% of the binding (IC50) to A type saliva at 2.6 µg/ml, respectively. For B type saliva IC50 values for Nano-26 were 4.3 µg/ml, respectively. Binding was expressed as a percentage of the untreated VLP binding (100%). All experiments were performed in triplicate (error bars are shown).

Figure 2:
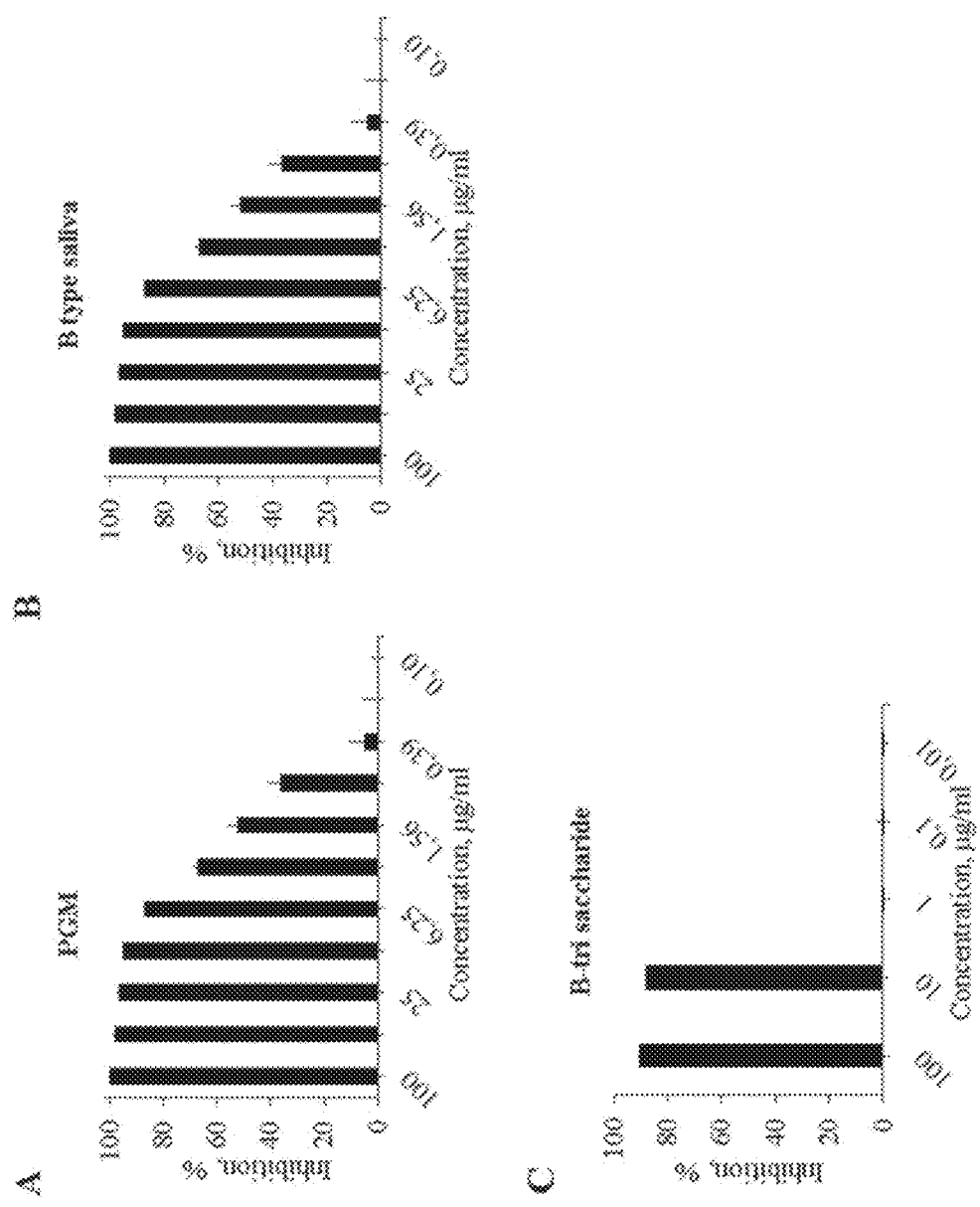

FIG. 2. Nano-26 inhibition of GII.4 VLP attachment to PGM, saliva and synthetic HBGAs. (A) Inhibition of GII.4 VLPs (0.5 µg/ml) binding to PGM. Nano-26 blocked GII.4 VLP binding with IC50 of 2.5 µg/ml. (B) Inhibition of GII.4 VLPs (0.5 µg/ml) binding to B type saliva. Nano-26 blocked GII.4 VLP binding with IC50 of 1.2 µg/ml. (C) Inhibition of GII.4 VLPs (0.5 µg/ml) binding to synthetic B-tri saccharide. Both Nano-26 showed a complete inhibition at 10 µg/ml and no inhibition at 1 µg/ml. Binding is expressed as a percentage of the untreated VLP binding (100%). All experiments were performed in triplicate (error bars are shown) and the cutoff was set at an OD490 of 0.15 (dashed line).

Figure 3:
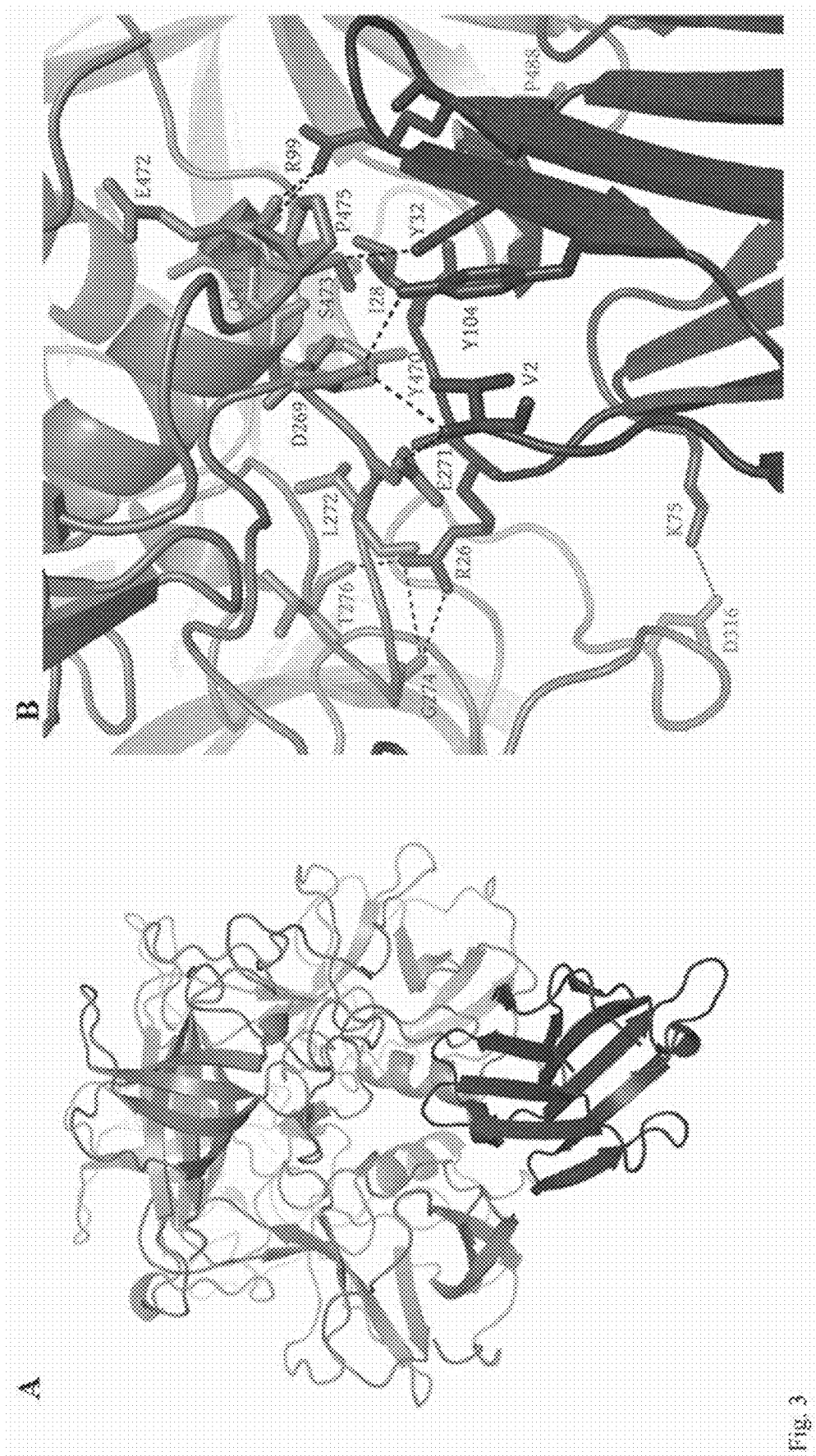

FIG. 3. Nanobody treatment of GII.10, GII.4 and GII.17 norovirus VLPs causes capsid deformation. GII.10, GII.4 and GII.17 VLPs were treated with each Nanobody for 1 h at room temperature and applied on EM grids for negative staining. Nano-26 binding caused changes in particle integrity. Negative stain EM images were obtained at 50,000 magnification. The scale bar represents ~50 nm.

Figure 4:
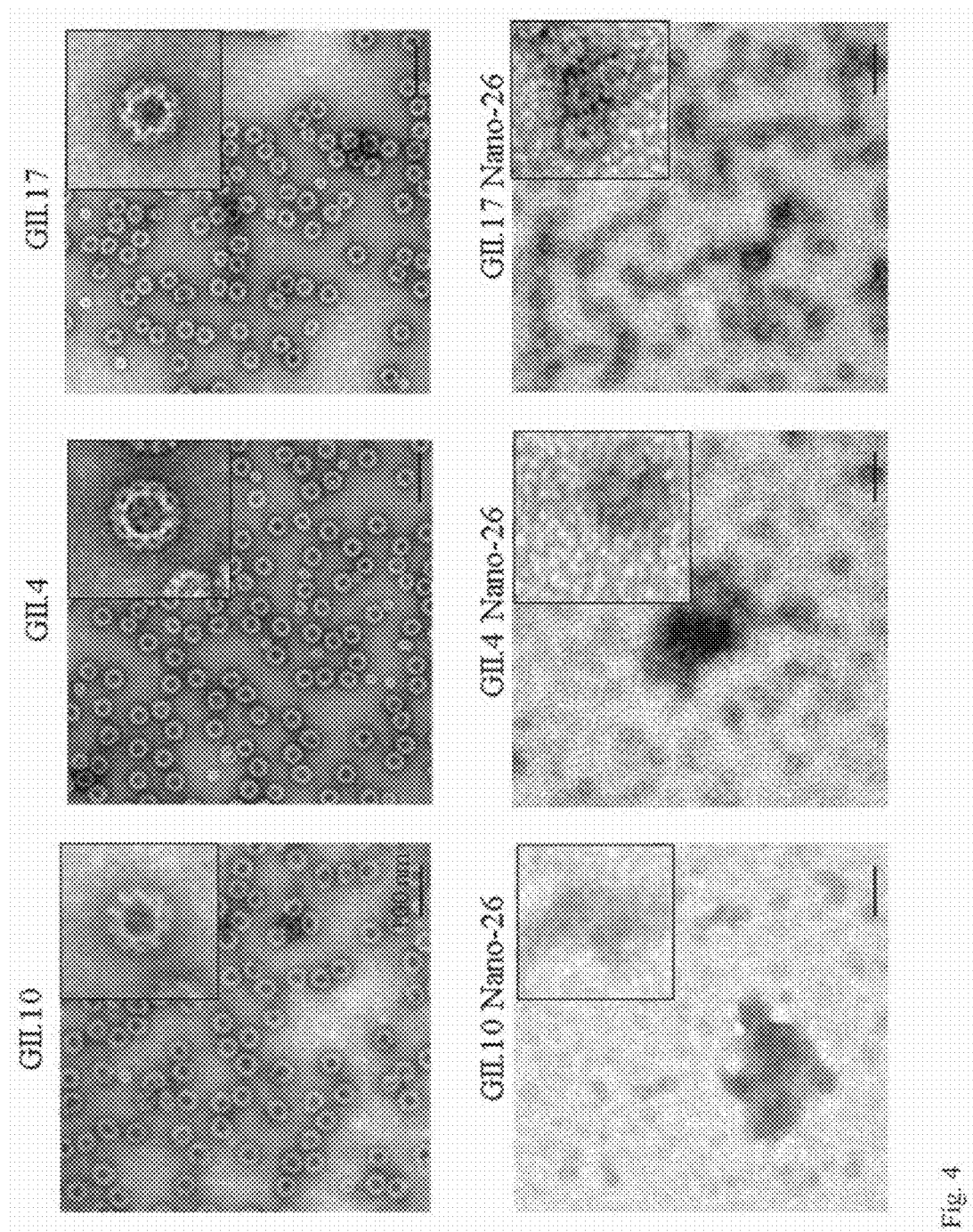

FIG. 4. Synergetic effect of Nano-85 and Nano-26. GII.10 VLPs were pre-incubated with Nano-85, Nano-26, or with both Nano-85 and Nano-26 for 30 min at room temperature. After treatment VLPs were subjected to negative staining and examined by EM at 50,000 magnification. VLPs exposed to Nano-85 showed a temperature dependence of morphological changes. At RT small 20-23 nm Nano-85 treated VLPs appeared and prevailed at 37° C. In case of Nano-26 and joint Nano-26 and Nano-85 treatment VLPs were largely degraded at any tested temperature.

Figure 5:
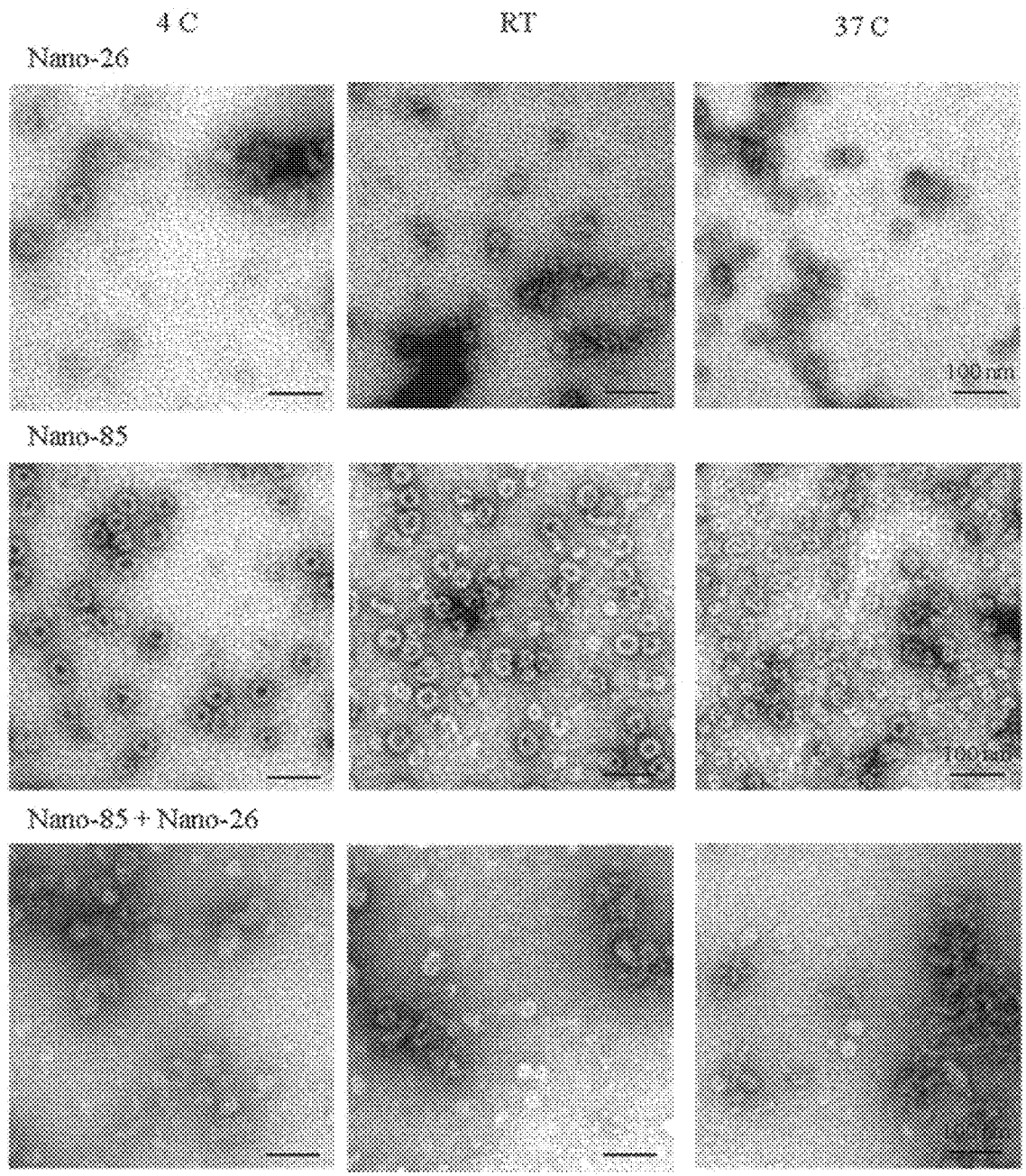

FIG. 5. Nano-26 Nano-85 GII.10 P domain double complex structure. GII.10 P domain Nano-26 Nano-85 crystal diffracted to 2.3 Å in a C121 space group. Unit cell contained a P domain dimer with two Nano-85 and two Nano-26 molecules. (A) GII.10 P domain is colored as in FIG. 3 with Nano-26 (cyan) and Nano-85 (orange). The Nano-85 and Nano-26 binding site in a double complex were identical to binding sites in individual complexes. (B) Nano-26 binds to the cleft between two P domain monomers at the bottom of the P domain dimer. (C) Close up view on the interactions between P domain residues and a Nano-26. Seven direct hydrogen bonds formed between P domain chain B: D269, L272, E274, E471, E472, T276 and Nano-26: V2, R26, R99, and Y104. P domain chain A: I231, P488 and chain B: E271, D316, Y470, and P475 were involved in hydrophobic interactions and two electrostatic interactions with Nano-26: V2, I28, F30, M31, K75, and A102.

Figure 6:
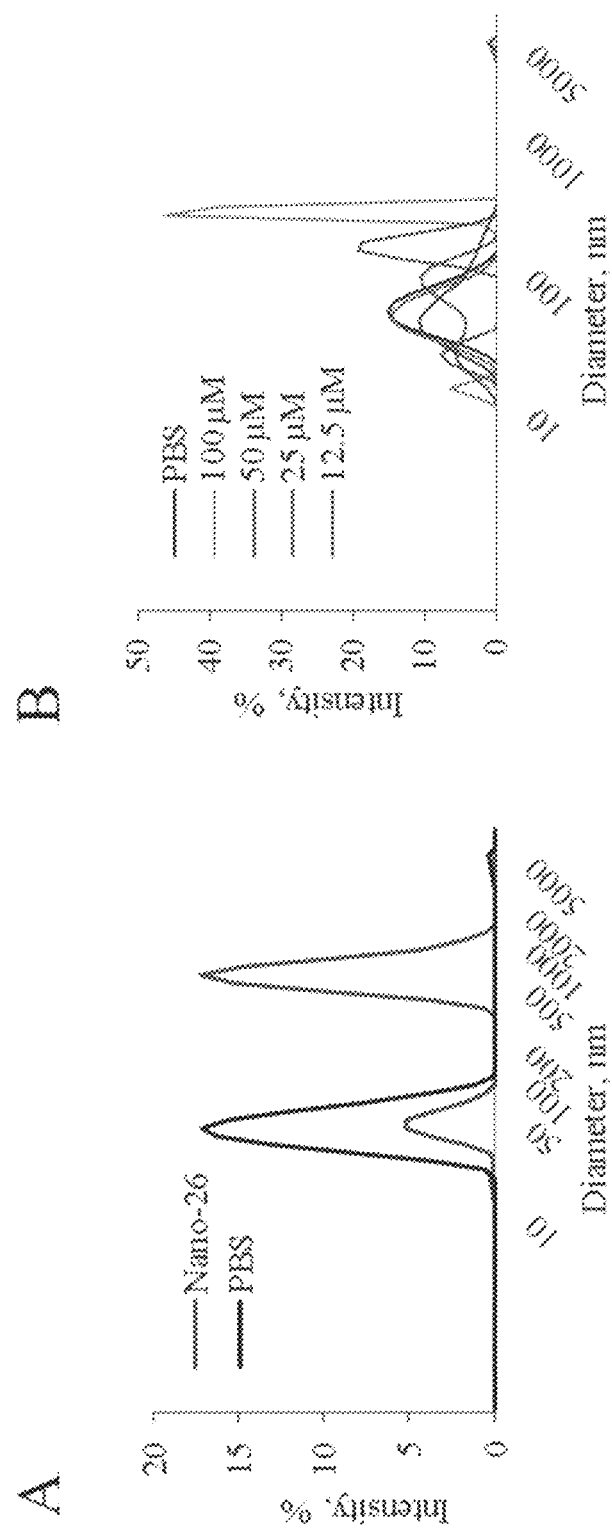

FIG. 6. Nanobody treatment leads to changes in norovirus capsid morphology. (A) DLS profiles of Nanobody treated GII.10 VLPs. Nano-26 binding caused the formation of large molecular weight aggregates. All experiments were performed in triplicates. (C) Additionally, GII.4 VLPs were pre-incubated with different concentrations of Nano-26 for one hour at RT. Size distribution was altered at concentrations over 12.5 µM for Nano-26.

Figure 7:
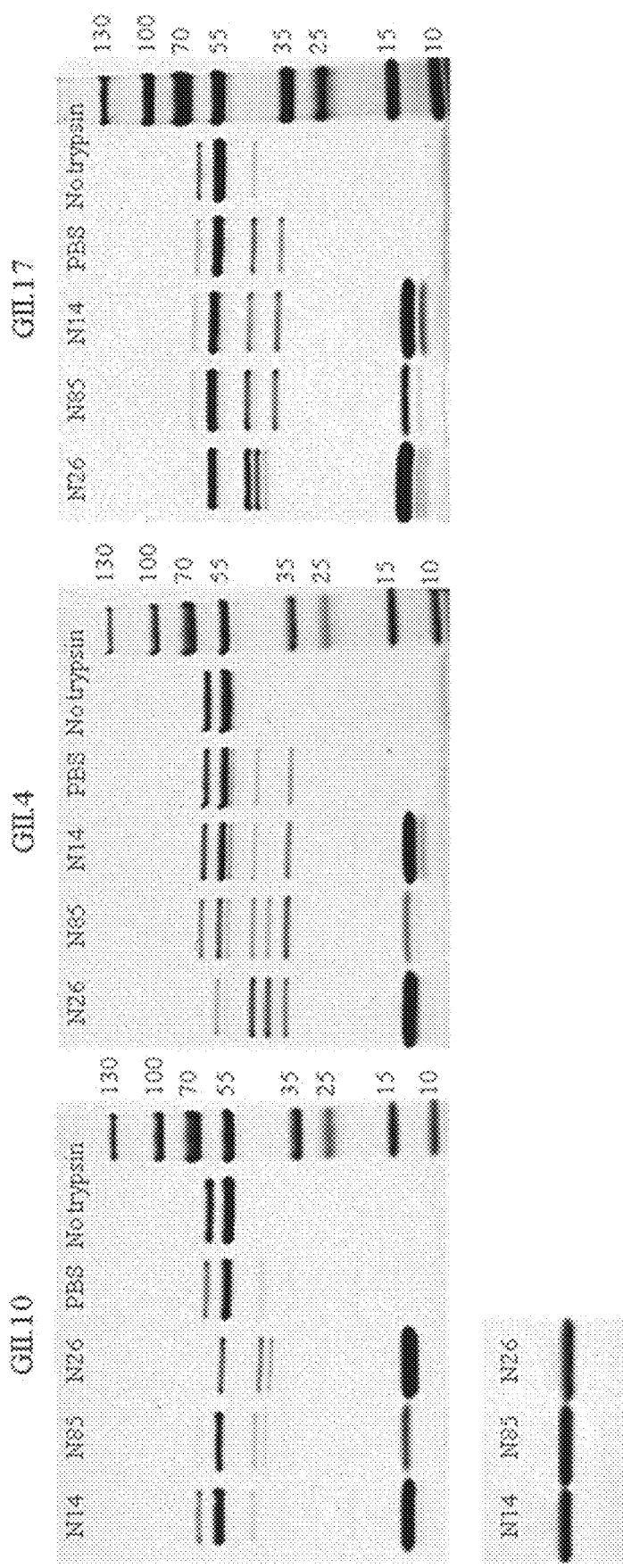

FIG. 7. Proteolytic digestion of norovirus VLPs. GII.10, GII.4, and GII.17 VLPs (1 mg/ml) were treated with 1 mg/ml of Nano-26 (lane N26), or PBS for 30 min at 37C. After the treatment samples were exposed to typsin (10 µg/ml final concentration) for additional 30 min at 37C. Samples were then run on the SDS PAGE and stained with Coomassie. VLPs without trypsin cleavage correspond to the lane VLPs. Nano-26 significantly increased the digestion efficiency.

Figure 8:
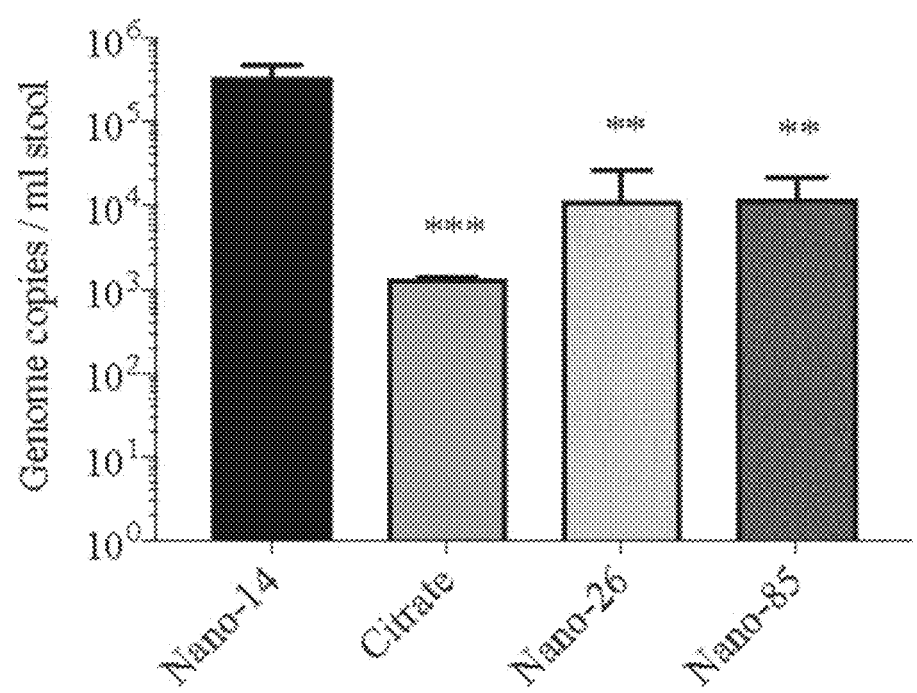

FIG. 8. Nano-26 treatment leads to RNA exposure. Concentrated stool suspension was treated with Nano-14, Nano-26, Nano-85, and 250 mM citrate buffer and subsequently with 50 u RNAse One. Genome copies were quantified with RT-qPCR. Nano-26, Nano-85, and citrate caused a significant decrease in genome copy levels compared to Nano-14. Statistical analysis was performed using one-way ANOVA test. Significant differences ($P \leq 0.05$) between the treated samples and a negative control (Nano-14 treatment) are marked with stars.

The following Examples shall merely illustrate the invention. They shall not be construed, whatsoever, to limit the scope of the invention.

EXAMPLES

Example 1: P Domain Production

The norovirus P domains, GI.1 (Norwalk virus, Genbank accession number M87661), GI.11 (Akabane, EF547396), GII.1 (Hawaii, U07611), GII.2 (Snow Mountain, AY134748), GII.4 (Sydney-2012, JX459908 and Saga4 2006, AB447457), GII.10 (Vietnam026, AF504671), GII.12 (Hiro, AB044366), and GII.17 (Kawasaki308, LC037415 were expressed in *E. coli*, purified and stored in GFB (25 mM Tris-HCl pH7.6, 0.3M NaCl) (Hansman G S, Natori K, Shirato-Horikoshi H, Ogawa S, Oka T, et al. (2006) Genetic and antigenic diversity among noroviruses. J Gen Virol 87: 909-919). The full-length capsid genes, GI.1 (AY502016.1), GI.11, GII.1, GII.2, GII.4, GII.10, GII.12, and GII.17, were expressed in insect cells using the baculovirus expression system and stored in PBS (Hansman G S, Natori K, Oka T, Ogawa S, Tanaka K, et al. (2005) Cross-reactivity among sapovirus recombinant capsid proteins. Arch Virol 150: 21-36; 5. Hansman G S, Saito H, Shibata C, Ishizuka S, Oseto M, et al. (2007) Outbreak of gastroenteritis due to sapovirus. J Clin Microbiol 45: 1347-1349).

Example 2: Generation of Norovirus Specific Nanobodies

Norovirus specific Nanobodies were produced at VIB Nanobody service facility, Belgium as previously described (Koromyslova A D, Hansman G S (2015) Nanobody binding to a conserved epitope promotes norovirus particle disassembly. J Virol 89: 2718-2730). Briefly, a single alpaca was injected with GII.10 VLPs. A VHH library was constructed from isolated peripheral blood lymphocytes and screened for the presence of antigen-specific Nanobodies using phage display. Thirty-five Nanobodies were isolated and allocated to 17 distinct groups based on a sequence alignment. The Nanobody genes were cloned to pHEN6C vector, expressed in WK6 *E. coli* cells, purified and stored in PBS or GFB.

Example 3: Direct Antigen ELISA

Nanobody titers to norovirus P domains or VLPs were quantified with direct ELISA (17). Briefly, microtiter plates were coated with 7 μg/ml of GII.10 P domains or 2 μg/ml of GII.10 VLPs. For cross-reaction experiments, 15 μg/ml P domain and 4 μg/ml VLPs were coated on ELISA plates. The VLPs or P domain were detected with serially diluted Nanobody and HRP-conjugated mouse α-His-tag monoclonal antibody. Absorbance was measured at 490 nm ($OD_{490}$) and all experiments were performed in triplicate.

Example 4: Blocking Assays

Pig gastric mucin (PGM) and saliva blocking assays were performed as previously described (Weichert S, Koromyslova A, Singh B K, Hansman S, Jennewein S, et al. (2016) Structural Basis for Norovirus Inhibition by Human Milk Oligosaccharides. J Virol 90: 4843-4848). Briefly, ELISA plates were coated with 10 μg/ml PGM (Sigma, Germany) or with saliva type A or B diluted in PBS 1:2000. Nanobody was two-fold serially diluted in PBS containing 2.5 μg/ml GII.10 VLPs (for PGM assay), 0.5 μg/ml GII.10 VLPs (for saliva assay) or 0.5 μg/ml GII.4 2006 VLPs (both PGM and saliva assay) and incubated for 1 h at RT. The VLPs-Nanobodies mixture was added to the plates and bound VLPs were detected with a α-GII.10 or α-GII.4 VLPs rabbit polyclonal antibody. For synthetic HBGA blocking assay, 10 μg/ml synthetic blood type B trisaccharide amine derivative (Dextra, UK) was coated on Pierce maleic anhydride activated plates (Thermo Fisher Scientific) overnight at 4C. Serially diluted Nanobody was pre-incubated with 5 μg/ml GII.4 VLPs for 1 h at RT. Following steps were performed as above. The binding of VLPs-only was set as a reference value corresponding to a 100% binding. The half maximal inhibitory concentrations ($IC_{50}$) values for Nanobody inhibition were calculated using GraphPad Prism (6.0a).

Example 5: Isothermal Calorimetry Measurements

Isothermal Calorimetry (ITC) experiments were performed using an ITC-200 (Malvern, UK). Samples were dialyzed into the identical buffer (GFB or PBS) and filtered prior titration experiments. Titrations were performed at 25° C. by injecting consecutive (1-2 μl) aliquots of Nano-26 (100-150 μM) into P domain (10-20 μM) with 150 second intervals. The binding data was corrected for the heat of dilution and fit to a one-site binding model to calculate the equilibrium binding constant, $K_A$, and the binding parameters, N and ΔH. Binding sites were assumed to be identical.

Example 6: P Domain and Nanobody Complex Purification and Crystallization

P domain and Nanobody complexes were purified by size exclusion chromatography (Koromyslova A D, Hansman G S (2015) Nanobody binding to a conserved epitope promotes norovirus particle disassembly. J Virol 89: 2718-2730). The GII.10 P domain Nano-26/Nano-85 complex was crystallized using the following conditions: 0.1 M sodium citrate, 40% (w/v) PEG600. Crystals were grown in a 1:1 mixture of the protein sample and mother liquor at 18° C. Prior to data collection, crystals were transferred to a cryoprotectant containing the mother liquor in 30% ethylene glycol, followed by flash freezing in liquid nitrogen.

Example 7: Data Collection, Structure Solution, and Refinement

X-ray diffraction data were collected at the European Synchrotron Radiation Facility, France at beamline BM30, ID30 Å, ID23-1 A and processed with XDS (Kabsch W (2010) XDS. Acta Cryst D66: 125-132). Structures were solved by molecular replacement in PHASER Phaser-MR (McCoy A J G-KR, Adams P D, Winn M D, Strone L C, Read R J. (2007) Phaser crystallographic software. Journal of Applied Crystallography 40: 658-674) using GII.10 P domain (PDB ID 3ONU) or GII.17 P domain (5F4M) and a Nano-85 (4X7D) as search models. Structures were refined in multiple rounds of manual model building in COOT (Emsley P L B, Scott W G, Cowtan K. (2010) Features and development of Coot. Acta Crystallographica Section D: Biological Crystallography 66: 486-501) and refined with PHENIX (Adams P D, Afonine P V, Bunkoczi G, Chen V B, Davis I W, et al. (2010) PHENIX: a comprehensive Python-based system for macromolecular structure solution. Acta Crystallographica Section D 66: 213-221). Alternative binding interfaces derived from the crystal packing were analyzed using an online server PDBePISA. The orientation of the Nanobody with the highest interface surface area and contact with CDRs was selected as the biologically relevant interface. Atomic coordinates were deposited to the Protein Data Bank (PDB).

Example 8: Electron Microscopy and Dynamic Light Scattering

The norovirus VLP morphology was analyzed using negative stain electron microscopy (EM) as previously described (Koromyslova A D, Hansman G S (2015) Nanobody binding to a conserved epitope promotes norovirus particle disassembly. J Virol 89: 2718-2730). Nanobodies (1 mg/ml) and VLPs (1 mg/ml) were mixed in 1:1 ratio and incubated for 1 h at room temperature. Prior to loading on carbon coated EM grids, all samples were diluted 30 times with distilled water. Grids were washed two times with distilled water and stained with 1% uranyl acetate. The grids were examined on a Zeiss 910 electron microscope (Zeiss, Oberhofen, Germany) at 50,000-fold magnification. VLP diameter was measured with ImageJ software using calibrated pixel/nm scale bar. The hydrodynamic diameters of treated and untreated norovirus VLPs were measured using dynamic light scattering (DLS) on ZetaSizer Nano (Malvern Instruments, UK). Samples were diluted 1:50 with PBS up to a final volume of 1 ml. Three x 12 measurement runs were performed with standard settings (Refractive Index 1.331, viscosity 0.89, temperature 25° C.). The average result was created with ZetaSizer software.

Example 9: Stool Treatment and Real-Time PCR

In order to determine the effects of the Nanobodies on native virions, we collected GII.4 positive stool samples from two individuals with acute norovirus infection (Doerflinger S Y, Weichert S, Koromyslova A, Chan M, Schwerk C, et al. (2017) Human Norovirus Evolution in a Chronically Infected Host. mSphere 2(2):e00352-16). A 10% (w/v) stool suspension was prepared in PBS and clarified by centrifugation at 10,000×g for 10 min. First stool sample was concentrated by ultracentrifugation at 285000×g for three hours. Then, 70 μl of the supernatant were treated with 150 μl of each Nanobody (1 mg/ml) for 30 min at room temperature. Samples were digested with 50 units RNAse One (Promega, Germany) for 30 min at 37° C. After treatment total RNA was extracted with QIAamp Viral RNA extraction kit (Qiagen, Hilden, Germany). One step RT-qPCR was performed with previously published GII.4 primers NKP2F (ATG TTY AGR TGG ATG AGA TTC TC) (SEQ ID NO:20), NK2R (TCG ACG CCA TCT TCA TTC ☒ AC☒) (SEQ ID NO:21), and probe RING2-TP (5'-FAM-TGG GAG GGC GAT CGC AAT ☒ CT-TAMRA-3'☒) (SEQ ID NO:22) using qScript™ XLT One-Step RT-qPCR ToughMix (Quantabio, USA). Viral load was quantified by comparison to a standard curve of GII.4 norovirus RNA transcripts of a known concentration. Average values for three independent experiments are presented. Statistical analysis was performed using one-way ANOVA test. Differences were considered significant when $P \leq 0.05$.

Example 10: Trypsin Digestion

To evaluate the impact of Nanobody binding on capsid susceptibility to proteolytic digestion norovirus VLPs (1 mg/ml) were incubated with Nanobodies (1 mg/ml) in 1:1 ratio for 30 min at 37° C. Then, trypsin-EDTA was added to final concentration of 10 μg/ml for 30 min at 37° C. The concentration of trypsin was chosen to yield only partial cleavage with visible intermediate products. After digestion, samples were loaded on the SDS-12% polyacrylamide gel and stained with coomassie stain.

Example 11: Binding Specificities

The Nanobody binding specificities were initially confirmed with the immunization antigen (i.e., GII.10 VLPs) and the corresponding GII.10 P domain. Nano-26 showed strong binding capacity to both P domain and VLPs (~50 ng/ml). Following these results, the cross-reactivity was analyzed with a panel of VLPs and P domains from various GI (GI.1 and GI.11) and GII (GII.1, GII.2, GII.4 2006 and 2012, GII.10, GII.12, and GII.17) genotypes (FIG. 1A). Nano-26 showed broad reactivity, detecting all GII genotypes.

Example 12: HBGA Blocking Properties of Nanobodies

In order to determine the HBGA blocking potential of the Nano-26, a surrogate neutralization assays were performed using GII.10 and GII.4 VLPs. Nano-26 inhibited the binding of GII.10 VLPs to PGM in a dose-dependent manner ($IC_{50}=6.6$ μg/ml) (FIG. 1). Similarly, Nano-26 inhibited binding to A-type saliva ($IC_{50}=3.1$ μg/ml) and B-type saliva ($IC_{50}=4.3$ μg/ml) (FIGS. 1C and 1D). Additionally, Nano-26 blocked GII.4 VLPs from binding to PGM (FIG. 2A) ($IC_{50}$ 2.4 μg/ml) and B-type saliva ($IC_{50}$ 0.7 μg/ml) (FIG. 2B). To demonstrate that Nano-26 specifically inhibit VLP binding to HBGAs present in PGM and saliva, a blocking assay using synthetic HBGAs was performed (FIG. 2C). Nano-26 blocked GII.4 VLPs from binding to synthetic B-tri saccharide with $IC_{50}$ ranging between 1 μg/ml to 10 μg/ml.

Example 13: Thermodynamic Properties

The thermodynamic properties of Nanobody binding to GII.10 P domain were analyzed using ITC. Nano-26 exhibited exothermic binding with nanomolar affinity $K_d$ (3.20E-09, M), ΔH (−1.00E+04, cal/mole), ΔS (4.8, cal/mole/deg), ΔG (change in free energy, cal/mol). The binding reaction was driven by a large enthalpy change and was characterized with unfavorable entropy of the binding. This suggested that the net formation of non-covalent bonds between the Nanobody and the P domain was a major contributor to the binding. The stoichiometry indicated the binding of one Nanobody molecule per P domain monomer.

Example 14: X-Ray Crystal Structures of Norovirus P Domain Nanobody Complex

We solved a double complex structure of GII.10P domain with Nano-26/Nano-85, which permitted a higher resolution than the GII.10 P domain and Nano-26 complex alone, and explained how two distinct Nanobodies bound simultaneously to one P dimer (Table 1). The overall structure of the P domains in all complex structures was reminiscent of unbound P domain. Nano-26 had typical immunoglobulin fold and interacted with the P domain primarily with CDR loops. The electron density for Nano-26 was well resolved.

TABLE 1

Data collection and refinement statistics for P domain Nanobody complex structures.

| | Nano-26 Nano-85 GII.10 P domain |
|---|---|
| PDB | 5O04 |
| Data collection | |
| Space group | C121 |
| Cell dimensions | |
| a, b, c (Å) | 167.2 91.5 118.1 |
| α, β, γ (°) | 90 127.12 90 |
| Resolution range (Å) | 47.98-2.30 (2.44-2.30)* |
| $R_{merge}$ | 7.9 (59.2)* |
| I/σI | 10.7 (2.3)* |
| Completeness (%) | 91.7 (90.1)* |
| Redundancy | 2.8 (2.7)* |
| CC½ | 99.6 (76.3) |
| Refinement | |
| Resolution range (Å) | 47.98-2.30 |
| No. of reflections | 58206 |
| $R_{work}/R_{free}$ | 21.2/24.1 |
| No. of atoms | 8217 |
| Protein | 8064 |
| Ligand/ion | 72 |
| Water | 81 |
| Average B factors (Å$^2$) | |
| Protein | 52.30 |
| Ligand/ion | 56.80 |
| Water | 38.20 |
| RMSD | |
| Bond lengths (Å) | 0.002 |
| Bond angles (°) | 0.67 |

Each data set was collected from single crystals, respectively.
*Values in parentheses are for the highest-resolution shell.

Example 15: Structure of GII.10 P Domain Nano-26 Nano-85 Double Complex

Nanobodies were previously shown to aid the crystallization process by increasing protein stability and stabilizing flexible regions (Korotkov K V, Pardon E, Steyaert J, Hol W G (2009) Crystal structure of the N-terminal domain of the secretin GspD from ETEC determined with the assistance of a nanobody. Structure 17: 255-265). We have already utilized Nano-85 to obtain high-resolution complex structures with three different norovirus P domains (Koromyslova A D, Hansman G S (2015) Nanobody binding to a conserved epitope promotes norovirus particle disassembly. J Virol 89: 2718-2730). Herein, we used Nano-85 to improve the resolution of the GII.10 P domain Nano-26 complex structure and describe the synchronized binding of two Nanobodies. The initial structure of GII.10 P domain Nano-26 complex was solved to ~3 Å resolution. A single crystal of GII.10 P domain Nano-85/Nano-26 double complex diffracted to 2.3 Å in C121 space group. Binding epitopes and interactions of both Nanobodies were identical to those in the individual complexes (ibd.). Nano-26 bound at the bottom of the P domain, perpendicular to Nano-85 binding site (FIG. 3).

Nano-26 binding site comprised of residues from both P domain monomers, although the majority of the P domain interactions involved only one chain (chain B). Nano-26 formed seven direct hydrogen bonds with one P domain monomer (chain B: Asp269, Leu272, Gly274, Gln471, Glu472, and Thr276) (FIG. 3B). Both P domain monomers were involved in hydrophobic interactions (chain A: Ile231, Pro488; and chain B: Tyr470 and Pro475) with Nano-26. In addition, two electrostatic interactions contributed to the tight binding. Nano-26 binding residues were mainly conserved between GII genotypes, which correlated well with the broad recognition shown with ELISA. Although the binding site was distant from the HBGA binding pocket, Nano-26 had a high inhibition capacity in the blocking assay, which also suggested indirect HBGA interference.

Example 16: VLP Structural Integrity Upon Nanobody Treatment

We previously showed that Nano-85 was able to disassemble norovirus VLPs (Koromyslova A D, Hansman G S (2015) Nanobody binding to a conserved epitope promotes norovirus particle disassembly. J Virol 89: 2718-2730) To explore if these six newly identified Nanobodies had a similar ability, we treated native-size VLPs with Nanobodies and examined the treated-particle morphology using EM. Similarly to Nano-85, Nano-26 treatment partially disassembled and deformed the native-size VLPs (FIG. 4). We also performed DLS measurements to quantitatively evaluate GII.10 VLP heterogeneity after Nanobody exposure. Nano-26 treated VLPs mainly formed VP1 protein aggregates, although a small peak corresponding to native-size particles remained. Overall, the DLS analysis corresponded well with the EM results and provided additional evidence that Nanobody treatment altered the capsid structural integrity.

To understand if these effects were relevant for clinically important norovirus strains, GII.4 (Sydney 2012) and GII.17 VLPs were treated with Nano-26 (FIG. 4). Nano-26 treatment lead to malformed and aggregated GII.4 VLPs and produced only a few small-size particles. In the case of GII.17 VLPs, caused the formation of small-size VLPs. Overall, these results suggested that effects of the Nanobody treatment might vary among different genotypes. To further evaluate the binding effects of Nano-26 on GII.4 (2012) VLPs, we performed concentration-dependent DLS measurements (S7 and S8 Figs). Nanobody effects were also concentration dependent, with minimum concentrations of 12.5 µM required for Nano-26 (S7C and D Figs). These results suggested that one Nano-26 molecule per VP1 dimer was sufficient to cause morphological changes.

To investigate a temperature dependence of the Nanobody treatment, we mixed GII.10 VLPs with Nano-85 and Nano-26 at 4° C., RT and 37° C. for 30 minutes (FIG. 5). Nano-85 treated VLPs showed a continuous degradation of native-size particles, producing small and/or partially broken particles as major intermediate forms. Nano-26 was more effective across the temperature range and almost completely altered the VLP integrity. The combination of Nano-85 and Nano-26 appeared to cause a more intense degradation of VLPs.

Example 17: Nanobody Effects on GII.4 Virions

In order to examine the Nanobody effects on norovirus virions, we implemented a modified RNA exposure assay and viral loads were quantified using real-time RT-PCR. Concentrated GII.4 positive stool samples were treated with the broadly reactive Nano-26 and Nano-85, while Nano-14 was used as a negative control and 250 mM citric buffer was used as a positive control. Treated samples were then subjected to RNAse One digestion. Nano-26, Nano-85, and citrate treated stool samples showed reduced genome copy numbers compared to the Nano-14 control (approx. 30 times for Nano-26 and Nano-85 and 250 times for citrate) (FIG. 10C). These results indicated that the Nano-26 and Nano-85 opened the virions and released the viral RNA, which was degraded by RNAse.

To further investigate if Nanobody treatment could render norovirus VLPs vulnerable to proteolytic cleavage, we subjected GII.10, GII.4, and GII.17 VLPs to a 30-minute trypsin digestion after Nanobody exposure and observed the protein bands using SDS-PAGE (S10 Fig). Nano-14 treated VLPs produced similar bands as the untreated VLPs. Nano-26 and Nano-85 treatment resulted in multiple cleavage products for GII.10 and GII.4 VLPs. In the case of GII.17 VLPs, only Nano-26 treatment showed additional cleavage of the capsid protein. Overall, these results suggested that Nano-85 and Nano-26 caused the particles to become structurally unstable, more vulnerable to proteolytic cleavage, and viral RNA exposure.

NON-STANDARD LITERATURE CITED IN THIS SPECIFICATION

Adams P D et al., Acta Crystallographica Section D 2010; 66:213-221
Crawford S E et al., Clin Vaccine Immunol. 2015; 22(2): 168-77
Doerflinger S Y et al. mSphere 2017; 2(2):e00352-16.
Emsley P et al., Acta Crystallographica Section D: Biological Crystallography 2010: 66:486-501
EP 0 404 097
EP 2 757 111 A1
Gabriel I. Parra et al. PLoS One. 2013; 8(6):e67592
Hansman G S et al. J Virol. 2012; 86(7):3635-46
Hansman, G S et al. J Gen Virol 2006; 87:909-91
Hansman G S et al. Arch Virol 2005; 150:21-36
Hansman G S et al., J Clin Microbiol 2007; 45:1347-1349.
Hollinger et al., PNAS USA 1993; 90:6444-6448
Hudson et al., Nat. Med. 2003; 9:129-134
Kabsch W, Acta Cryst 2010; D66:125-132
Koromyslova A D & Hansman G S, J Virol 2015; 89:2718-2730.
Korotkov K V et al. Structure 2009; 17:255-265
Kou B et al., Clin Vaccine Immunol. 2015; 22(2):160-7
Kroneman, A et al., Arch Virol 2013; 158:2059-2068
Li X et al., Virus Res. 2009; 140(1-2):188-93
Li X et al., Virus Res. 2010; 151(2):142-7
McCoy A J et al., Journal of Applied Crystallography 2007; 40: 658-674
Parker T D et al., J Virol. 2005; 79(12):7402-9
Prasad, B V et al., Science 1999, 286:287-290
Shiota T et al., J Virol. 2007; 81(22):12298-306
Smith, T J. et al, Curr Opin Virol 2011, 1:150-156
Weichert S et al., J Virol 2016; 90: 4843-4848.
WO 1993/01161
WO 2016/059113
Yoda T et al., J Clin Microbiol. 2003; 41(6):2367-71.

The invention claimed is:

1. A binding polypeptide specifically binding to an epitope comprised in an amino acid sequence corresponding to amino acids 250 to 300 of the norovirus genotype II.10 capsid polypeptide, wherein said binding polypeptide is a single-domain antibody (VHH) comprising the complementarity determining regions (CDRs) of SEQ ID NOs:13, 15, and 17.

2. The binding polypeptide of claim 1, wherein said epitope is comprised in the amino acid sequence corresponding to amino acids 260 to 280 of said norovirus capsid polypeptide.

3. The binding polypeptide of claim 1, wherein said epitope comprises the motif a-x-a-h-x-h-x-o (SEQ ID NO:5), with "x" being any amino acid; "a" being glutamic acid or aspartic acid; "h" being glycine, alanine, valine, leucine or isoleucine, and "o" being serine or threonine.

4. The binding polypeptide of claim 1, wherein said binding peptide further specifically binds to a second epitope comprised in an amino acid sequence corresponding to amino acids 450 to 490 of said norovirus genotype II.10 capsid polypeptide.

5. The binding polypeptide of claim 4, wherein said second epitope comprises the motif N or Q-D or E.

6. A composition comprising the binding polypeptide according to claim 1 and a carrier.

7. The composition of claim 6, wherein said composition further comprises Nano-85 specifically binding to an epitope comprised in the amino acid sequence of a norovirus capsid polypeptide.

8. The binding polypeptide of claim 5, wherein said second epitope comprises the motif Y-Q-E-S-x-P-$(x)_{12}$-P (SEQ ID NO:10).

9. The binding polypeptide of claim 1, wherein said binding polypeptide comprises an amino acid sequence having the amino acid sequence of SEQ ID NO:11 or comprises an amino acid sequence having at least 70% sequence identity to SEQ ID NO:11.

10. The composition of claim 6, wherein said composition is a pharmaceutical composition.

11. The composition of claim 7, wherein the Nano-85 specifically binds to the amino acid sequence W-V-N-x-F-Y-x (SEQ ID NO:19), with "x" being any amino acid.

12. A method, comprising
   contacting a subject and/or an object suspected to comprise a norovirus particle to a binding polypeptide according to claim 1.

* * * * *